(12) United States Patent
Choi

(10) Patent No.: US 9,076,310 B2
(45) Date of Patent: Jul. 7, 2015

(54) METHOD AND ELECTRONIC DEVICE FOR REMOTE DIAGNOSIS

(75) Inventor: Kyuhyoung Choi, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 222 days.

(21) Appl. No.: 13/813,376

(22) PCT Filed: Jul. 30, 2010

(86) PCT No.: PCT/KR2010/005056
§ 371 (c)(1),
(2), (4) Date: Jan. 31, 2013

(87) PCT Pub. No.: WO2012/015094
PCT Pub. Date: Feb. 2, 2012

(65) Prior Publication Data
US 2013/0127622 A1    May 23, 2013

(51) Int. Cl.
*G08B 23/00* (2006.01)
*G08B 5/22* (2006.01)
*G06Q 50/22* (2012.01)
*A61B 1/00* (2006.01)
*A61B 5/00* (2006.01)

(52) U.S. Cl.
CPC ... *G08B 5/22* (2013.01); *A61B 1/00* (2013.01); *A61B 5/00* (2013.01); *G06Q 50/22* (2013.01)

(58) Field of Classification Search
CPC .................................. A61B 1/00; A61B 5/00
USPC .......... 340/573.1; 600/437; 606/10.34; 601/2
See application file for complete search history.

(56) References Cited

U.S. PATENT DOCUMENTS

| | | | |
|---|---|---|---|
| 2003/0004502 A1* | 1/2003 | Clapham et al. | 606/10 |
| 2005/0020917 A1* | 1/2005 | Scherch | 600/437 |
| 2008/0275730 A1 | 11/2008 | Nam | |
| 2011/0201976 A1* | 8/2011 | Sanghvi et al. | 601/2 |
| 2011/0264088 A1* | 10/2011 | Orszulak | 606/34 |

FOREIGN PATENT DOCUMENTS

| | | |
|---|---|---|
| KR | 10-2003-0081883 A | 10/2003 |
| KR | 10-2009-0001625 A | 1/2009 |
| KR | 10-2010-0019084 A | 2/2010 |

* cited by examiner

*Primary Examiner* — Shirley Lu
(74) *Attorney, Agent, or Firm* — Birch, Stewart, Kolasch & Birch, LLP

(57) ABSTRACT

The present invention relates to a remote treatment method and an electronic device. More specifically, the present invention provides a remote treatment method and an electronic device that indicate a progress state of a checkup.

20 Claims, 23 Drawing Sheets

FIG. 8
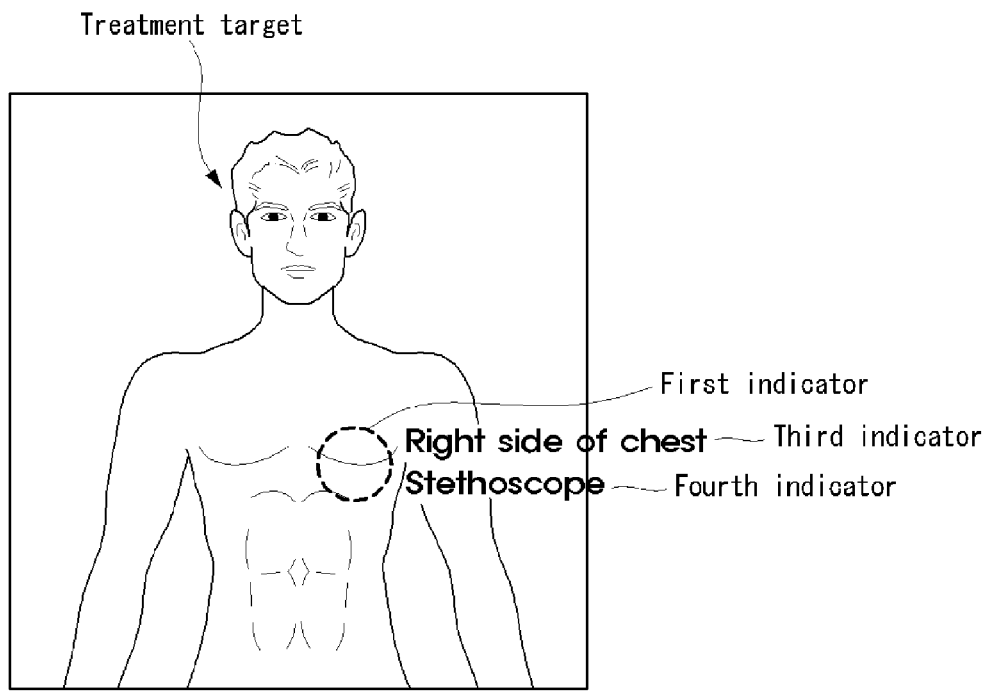
FIG. 9
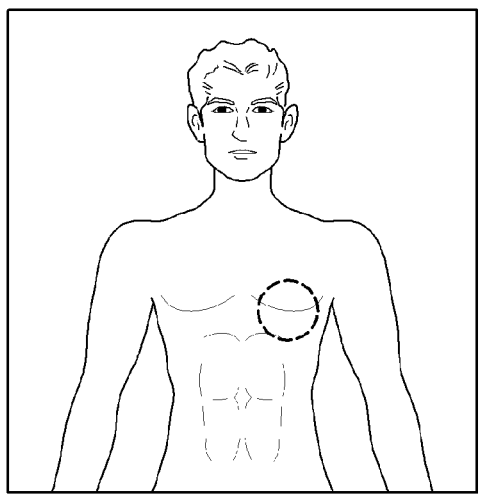
(a)
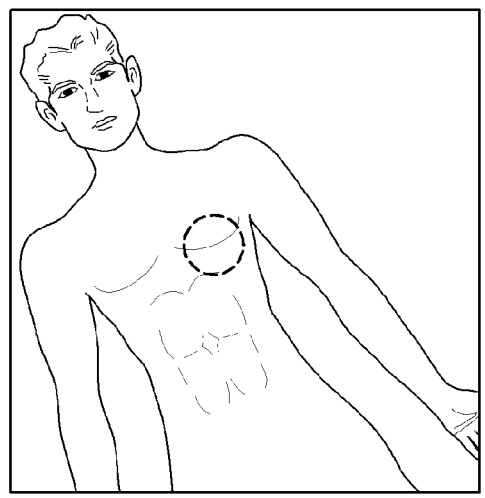
(b)

Second indicator

FIG. 32
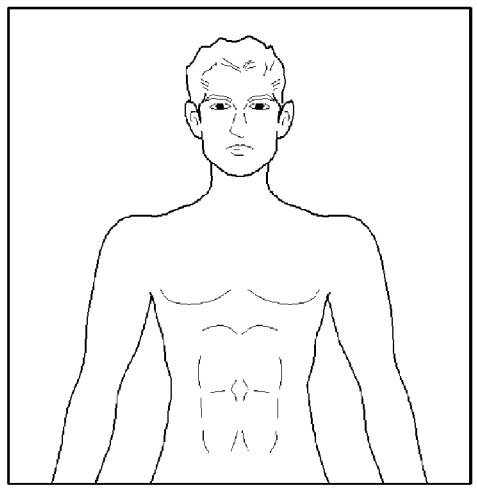
(a)
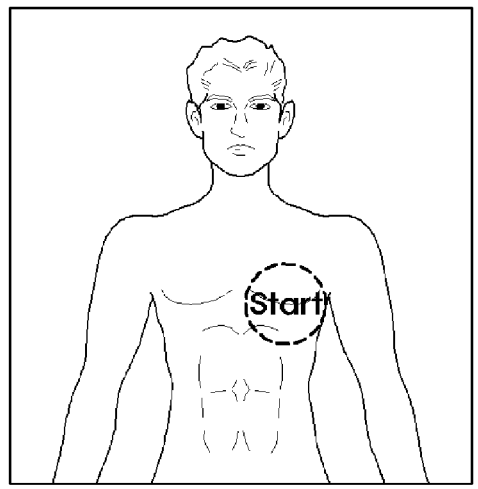
(b)
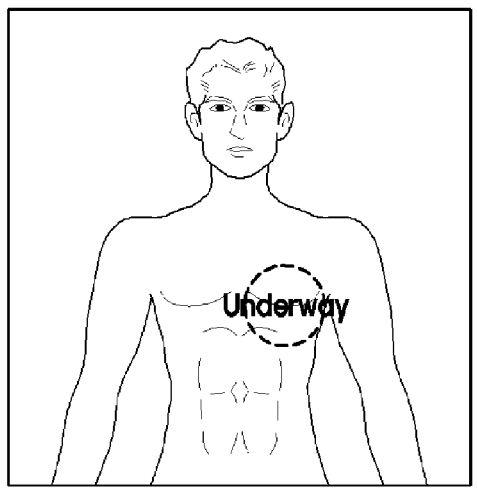
(c)
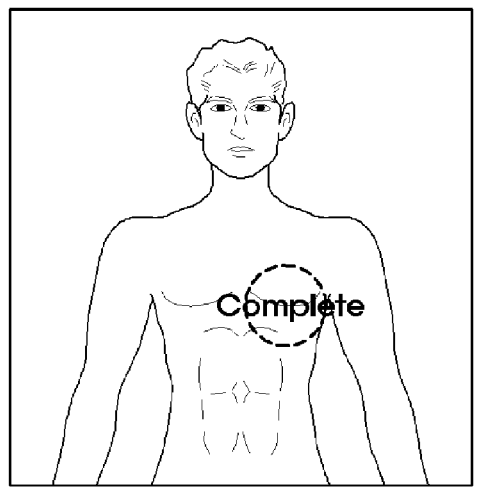
(d)

METHOD AND ELECTRONIC DEVICE FOR REMOTE DIAGNOSIS

BACKGROUND

1. Technical Field

The present invention concerns a remote treatment method and an electronic device. More specifically, the present invention is directed towards a remote treatment method and an electronic device that indicates a progress state of a checkup.

2. Discussion of the Related Art

Busy daily life renders it difficult for modern people to go to hospital for medical services, and thus, a need exists to provide medical services anytime, anywhere.

SUMMARY

The present invention has been designed to solve problems with the conventional remote treatment and provides the following objects.

An object of the present invention is to provide a remote treatment method and an electronic device that display a checkup part on an image of a treatment target.

Another object of the present invention is to provide a remote treatment method and an electronic device that guide a manipulation of a checkup tool.

Still another object of the present invention is to provide a remote treatment method and an electronic device that prevent a patient's personal information from being exposed.

Yet still another object of the present invention is to provide a remote treatment method and an electronic device that display a progress state of a treatment.

Yet still another object of the present invention is to provide allow a remote treatment to be effectively performed.

Technical objects of the present invention are not limited to those described above, and the above or other objects may be apparent to those skilled in the art from the detailed description.

The present invention achieves the above objects by providing the following motion guiding apparatus and motion guiding method.

An electronic device according to an aspect of the present invention includes an output unit that outputs an image of a treatment target, a communication unit that receives medical information including information regarding a checkup part of the treatment target from an external device, and a controller that obtains a first area corresponding to the checkup part in the image of the treatment target based on the received medical information and controls the output unit to display a first indicator reflecting the checkup part on the first area to overlap the output image of the treatment target.

An electronic device according to another aspect of the present invention includes an output unit that outputs an image of a treatment target, a communication unit that receives medical information including information regarding a checkup part of the treatment target from an external device, and a controller that obtains a first area corresponding to the checkup part in the image of the treatment target based on the received medical information and controls the output unit to display a first indicator reflecting the checkup part on the first area to overlap the output image of the treatment target. Here, the controller obtains information regarding a position of a checkup tool and controls the output unit to output an alarm signal when at least a portion of the checkup tool is included in the first area based on the information regarding the position of the checkup tool. The alarm signal includes at least one of a visual signal, an auditory signal, and a tactile signal.

An electronic device according to still another aspect of the present invention includes an output unit that outputs an image of a treatment target, a communication unit that receives medical information including information regarding a checkup part of the treatment target from an external device, and a controller that obtains a first area corresponding to the checkup part in the image of the treatment target based on the received medical information and controls the output unit to display a first indicator reflecting the checkup part on the first area to overlap the output image of the treatment target. Here, the controller obtains information regarding a position of a checkup tool and controls the output unit to output information for guiding a manipulation of the checkup tool based on a relative position between the position of the checkup tool and the first area. At this time, the information for guiding the manipulation of the checkup tool includes at least one of information indicating a pause of the checkup tool when the position of the checkup tool is substantially consistent with the first area and information indicating at least one of a shift direction and a shift distance of the checkup tool when the position of the checkup tool is substantially insistent with the first area.

An electronic device according to yet still another aspect of the present invention includes an output unit that outputs an image of a treatment target, a communication unit that receives medical information including information regarding a checkup part of the treatment target from an external device, and a controller that obtains a first area corresponding to the checkup part in the image of the treatment target based on the received medical information and controls the output unit to display a first indicator reflecting the checkup part on the first area to overlap the output image of the treatment target.

Here, the controller obtains information regarding a position of a checkup tool, obtains a second area corresponding to the position of the checkup tool in the image of the treatment target based on the information regarding the position of the checkup tool, and controls the output unit to display a second indicator reflecting the checkup tool on the second area to overlap the output image of the treatment target. Again, here, the information regarding the checkup part includes information regarding a name of the checkup part, and the controller controls the output unit to display a third indicator reflecting the name of the checkup part on the first area to overlap the output image of the treatment target based on the medical information. Again, here, the medical information further includes information regarding the type of the checkup tool, and the controller controls the output unit to display a fourth indicator reflecting the type of the checkup tool on the first area to overlap the output image of the treatment target based on the medical information.

An electronic device according to yet still another aspect of the present invention includes an output unit that outputs an image of a treatment target, a communication unit that receives medical information including information regarding a checkup part of the treatment target from an external device, and a controller that obtains a first area corresponding to the checkup part in the image of the treatment target based on the received medical information and controls the output unit to display a first indicator reflecting the checkup part on the first area to overlap the output image of the treatment target.

Here, the electronic device further includes an input unit that receives an input for selecting a partial image of the image of the treatment target, and the communication unit transmits the partial image to an external device, and the external device outputs only the partial image selected from the image of the treatment target. Again, here, the partial image includes at least one of an image regarding a partial area of the whole image of the treatment target and some frames of all the frames of the image of the treatment target.

An electronic device according to yet still another aspect of the present invention includes an output unit that outputs an image of a treatment target, a communication unit that receives medical information including information regarding a plurality of checkup parts from an external device, and a controller that obtains a plurality of first areas corresponding to the plurality of checkup parts in the image of the treatment target based on the medical information and controls the output unit to display a plurality of first indicators respectively reflecting the plurality of checkup parts on the plurality of first areas to overlap the output image of the treatment target. Here, the information regarding the plurality of checkup parts includes information regarding a checkup order of each of the plurality of checkup parts, and the controller controls the output unit to display a fifth indicator reflecting the checkup order of the plurality of checkup parts on the plurality of first areas to overlap the output image of the treatment target based on the medical information. Again, herein, the controller controls the output unit to delete a first indicator corresponding to a checkup part where the checkup has been complete among the plurality of first indicators.

A remote treatment method according to an aspect of the present invention includes the steps of outputting an image of a treatment target, receiving medical information including information regarding at least one checkup part from an external device, obtaining at least one first area corresponding to at least one checkup part in the image of the treatment target based on the medical information, and displaying at least one first indicator reflecting at least one checkup part on at least one first area to overlap the output image of the treatment target.

An electronic device according to another aspect of the present invention includes an output unit that outputs an image of a treatment target and a controller that displays an indicator reflecting a progress state of a treatment for the treatment target considering an attribute of the indicator and changes the attribute of the indicator based on the progress state.

An electronic device according to still another aspect of the present invention includes an output unit that outputs an image of a treatment target, a communication unit that receives information regarding the progress state of the treatment from at least one of an external device and a checkup tool, and a controller that displays an indicator reflecting a progress state of a treatment for the treatment target considering an attribute of the indicator and changes the attribute of the indicator based on the progress state.

An electronic device according to yet still another aspect of the present invention includes an output unit that outputs an image of a treatment target and a controller that displays an indicator reflecting a progress state of a treatment for the treatment target considering an attribute of the indicator and changes the attribute of the indicator based on the progress state. Here, the controller changes the attribute of the indicator so that the indicator is output when the treatment is started, changes the attribute so that when the treatment is in progress the indicator indicates that the treatment is in progress, and changes the attribute so that when an error occurs, the indicator indicates occurrence and cause of the error, and changes the attribute so that when the treatment is completed the indicator is not output.

An electronic device according to yet still another aspect of the present invention includes an output unit that outputs an image of a treatment target and a controller that displays an indicator reflecting a progress state of a treatment for the treatment target considering an attribute of the indicator and changes the attribute of the indicator based on the progress state. Here, the attribute of the indicator includes information regarding an output position of the indicator, and the output position is a position corresponding to the checkup part in the image of the treatment target. The controller controls the output unit so that the indicator is output to overlap the image of the treatment target.

A remote treatment method according to yet still another aspect of the present invention includes the steps of outputting an image of a treatment target, obtaining information regarding a progress state of the treatment for the treatment target, outputting an indicator reflecting the progress state of the treatment for the treatment target together with the image considering an attribute of the indicator, and changing the attribute of the indicator output based on the progress state of the treatment for the checkup part.

An electronic device according to yet still another aspect of the present invention includes an output unit that outputs an image of a treatment target, a communication unit that communicates with at least one of a checkup tool that treats the treatment target and an external device, and a controller that receives checkup part information from the external device through the communication unit, controls the output unit to display an indicator on the checkup part on the output image of the treatment target based on the checkup part information, and receives checkup data regarding the checkup part displayed by the indicator from the checkup tool through the communication unit. The checkup data includes at least one of bio-information measured from the checkup part and an affected part image obtained by capturing the checkup part.

An electronic device according to yet still another aspect of the present invention includes an output unit that outputs an image of a treatment target, a communication unit that communicates with at least one of a checkup tool that treats the treatment target and an external device, a storage unit that stores at least a portion of the image of the treatment target, and a controller that receives checkup part information from the external device through the communication unit, controls the output unit to display an indicator on the checkup part on the output image of the treatment target based on the checkup part information, and receives checkup data regarding the checkup part displayed by the indicator from the checkup tool through the communication unit.

The present invention has the following effects.

According to the present invention, a user may easily manipulate a checkup tool based on a checkup part displayed on an image of a treatment target when a remote treatment is performed.

According to the present invention user is specifically guided to manipulate a checkup tool himself/herself may perform a checkup even without specialized knowledge on the checkup tool when a remote treatment is performed.

According to the present invention user may be aware of the degree at which a checkup is in progress through a video treatment.

According to the present invention, a part which a user wants to be viewed in an image of a treatment target may be selectively used, thus protecting the user's privacy.

According to the present invention, a remote treatment may be performed more effectively, thus saving time and costs required for the treatment.

According to the present invention, a remote treatment may be smoothly performed, thus contributing to people's health and saving unnecessary medical costs.

BRIEF DESCRIPTION OF THE DRAWINGS

FIG. 8 is a view illustrating a first graphic user interface of a remote treatment method according to a first embodiment of the present invention.

FIG. 9 is a view illustrating a second graphic user interface of the remote treatment method according to the first embodiment of the present invention.

FIG. 32 is a view illustrating a first graphic user interface of the remote treatment method according to the eighth embodiment of the present invention.

DESCRIPTION OF THE EMBODIMENTS

The terms used herein are provided to readily describe the present invention.

Accordingly, the present invention is not limited by the terms used herein.

Various modifications or variations may be made to the present invention without departing from the spirit and scope of the present invention.

At this time, the modifications or variations made to the present invention without departing from the spirit and scope of the present invention are apparent to those skilled in the art. Accordingly, the present invention includes modifications or variations that do not depart from the spirit and scope of the present invention.

The same denotations are used to indicate the same elements, and repetitive description thereof may be skipped.

The present invention is not limited to the embodiments.

The present invention is hereinafter described with reference to the accompanying drawings.

Social progress gradually directs more concern toward personal health issues, and such tendency prompts demand for medical services. However, modern people's busy life is an obstacle to getting medical services by direct visit to a hospital, and thus, a need for anytime and anywhere medical treatment is suggested.

Recent advance in communication technologies brings more attention to remote treatment rather than the conventional face-to-face treatment. The "remote treatment" means that medical treatment is done by using communication means from a remote site without a face-to-face contact between a doctor and a patient. Such remote treatment may drastically save time and costs consumed for a round trip to a hospital, and overcome spatial, temporal, and economical limitations that are put to the treatment. In particular, the remote treatment may provide medical profits to patients with chronic disease or elderly people who require periodic treatment as well as people who reside in doctorless villages, islands, or separated towns which seldom reach medical services, and thus, gains attention as a next-generation industry.

However, in contrast to the conventional face-to-face treatment, the remote treatment cannot place a direct medical checkup on a patient's body and this is an obstacle to precise treatment. This is why a doctor need generally use dedicated tools for checkup of a patient's body, but the remote treatment cannot give a chance to the doctor for him to manipulate the medical tools. In the conventional remote treatment, some of the checkup processes are done by the patient himself following the doctor's indications, but handling of the medical tools requires medial knowledge and experience. Accordingly, the conventional remote treatment suffers from more time being consumed than when a doctor himself treats the patient and low accuracy rendering it difficult to provide efficient treatment.

Figure 1:
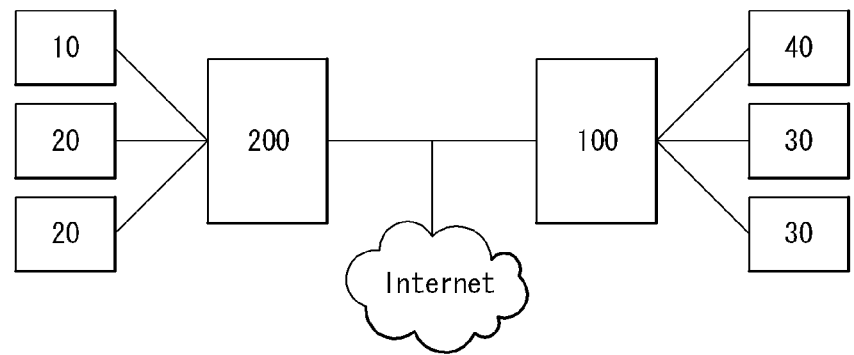
FIG. 1 is a view illustrating a configuration of a remote treatment system according to the present invention.
Figure 2:
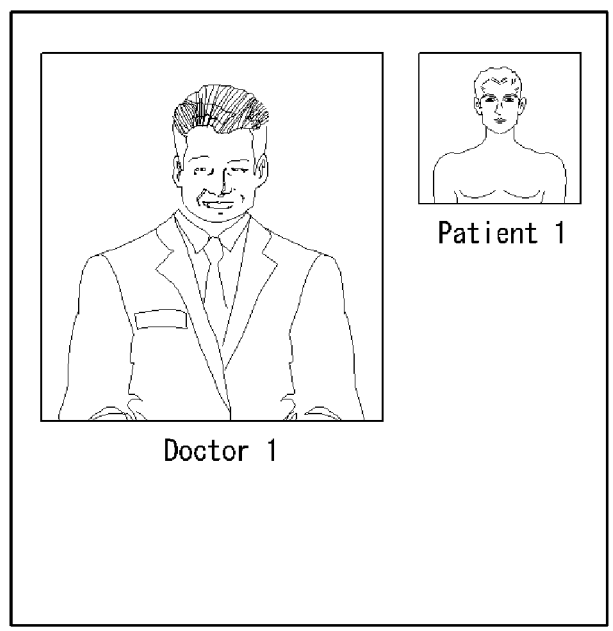
FIG. 2 is a view illustrating a graphic user interface (GUI) of a patient terminal according to an embodiment of the present invention.
Figure 3:
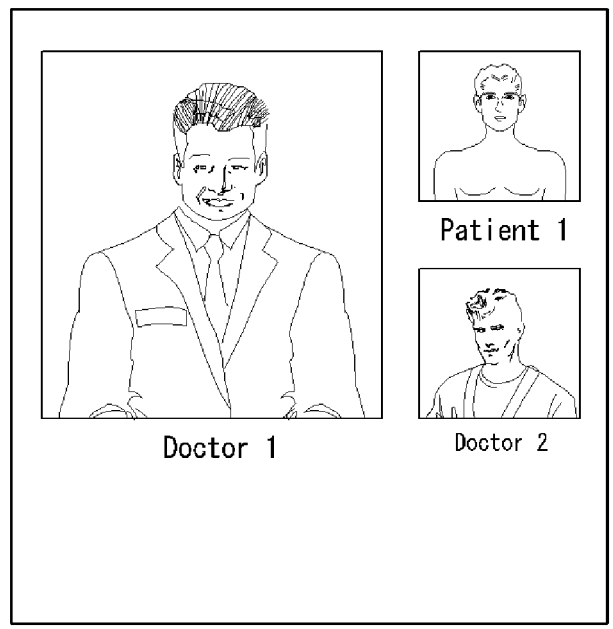
FIG. 3 is a view illustrating a graphic user interface of a patient terminal according to another embodiment of the present invention.

Hereinafter, a remote treatment system according to the present invention is described with reference to FIGS. 1, 2, and 3. FIG. 1 is a view illustrating a configuration of a remote treatment system according to the present invention, and FIGS. 2 and 3, respectively, are views illustrating graphic user interfaces of a patient terminal 100 according to an embodiment of the present invention.

The remote treatment system may be a system that allows a patient to receive a treatment from a medical person residing in a remote site by using a communication means. Here, the "patient" does not necessarily mean a person with a disease, but rather needs to be broadly construed as including any target for a treatment. Further, the patient is not limited to a person and may include an animal. Here, the "medical person" may include at least one of a medical doctor, a hospital, a pharmacist, a pharmacy, a medical consultant, a health manager, and a veterinarian.

As shown in FIG. 1, the remote treatment system may include at least one of a medical person terminal 200, a patient terminal 100, an assistant medical person terminal 20, a checkup tool 30, a server 10, and a personal portable terminal 40.

Here, the medical person terminal 200 and the patient terminal 100 may transmit and receive medical information for remote treatment to/from each other. A medical person and a patient may use the medical person terminal 200 and the patient terminal 100, respectively, so as to perform a remote treatment. The assistant medical person terminal 20 may be used for a joint treatment and allows another medical person to participate in the remote treatment. The server 10 may manage various medical information and provide medical information to the doctor's terminal to assist in the doctor's treatment. The checkup tool 30 may obtain information for a treatment, such as a precision image of an affected part of the patient or the patient's bio-information and may provide the information to the patient terminal 100. The personal portable terminal 40 may receive a result of the remote treatment so that the patient may easily identify the result anytime and anywhere.

Hereinafter, a configuration of the remote treatment system is described.

The medical person terminal 200 and the patient terminal 100 may be used by the medical person and the patient, respectively. The medical person terminal 200 and the patient terminal 100 may exchange various information including medical information through the Internet or other wired/wireless communication networks and may provide the information to the medical person and the patient, respectively. Accordingly, the medical person and the patient may perform a remote treatment by using their respective terminals.

For example, the medical person terminal 200 may receive the patient's image from the patient terminal 100, and the patient terminal 100 may receive the medical person's image from the medical person terminal 200. Here, as shown in FIG. 2, the medical person and the patient may perform a remote video treatment by their terminals providing corresponding images to the medical person and the patient. Through such video treatment, a remote site may also receive a medical service similar to a face-to-face treatment.

As another example, the patient terminal 100 may obtain bio-information from the checkup tool 30 and may provide the bio-information to the medical person terminal 200, which may then provide the information to the medical person. By doing so, the medical person may obtain information regarding the patient through a communication network at a remote site and may conduct a diagnosis.

Further detailed description of the medical person terminal 200 will be given below.

The assistant medical person terminal 20 may be used for a joint treatment. The assistant medical person terminal 20 may provide and receive medical information to/from the above-described medical person terminal 200 and the patient terminal 100 through the Internet or other wired/wireless communication networks. For example, as shown in FIG. 3, the medical person terminal 200, the patient terminal 100, and the assistant medical person terminal 20 may share the medical person's image, the patient's image, and other medical person's image and may provide the shared images to a user. by using the assistant medical person terminal 20, a plurality of medical persons may exchange their opinions with each other when performing a treatment, thus leading to a further effective temperature.

Meanwhile, the assistant medical person terminal 20 is not necessarily connected to both the medical person terminal 200 and the patient terminal 100, and may be connected only to the medical person terminal 200. For example, after a remote treatment between the medical person and the patient is terminated, the medical person may communicate with the assistant medical person terminal 20 through the medical person terminal 200 to thereby obtain another medical person's opinion. By doing so, the medical person may conduct a more precise diagnosis by referring to the other medical person's opinion.

The checkup tool 30 may obtain checkup data for a treatment from the patient. The checkup tool 30 may include a thermometer, a stethoscope, a blood pressure meter, a blood-sugar meter, an ECG meter, a camera, a body fat measuring device, an arteriosclerosis diagnostic device, an ultrasonic scanning apparatus, a urine tester, a pulsimeter, a blood collecting device, an X-ray device, an oxygen saturation tester, a dementia tester, a CAT (Computerized Axial Tomography) device, an MRI (Magnetic Resonance Imaging) device, an endoscope, a magnifying glass, and a camera-integrated magnifying glass. The checkup tool 30 may obtain checkup data including at least one of bio-information and an affected part image obtained by capturing a body part for treatment. Such information may include, e.g., a blood pressure, a body temperature, a pulse rate, a blood sugar, an ECG (ElectroCardioGram), an auscultation result, a precision image, an X-ray image, and an MRI image.

The checkup tool 30 may transmit the obtained information to an external device. Here, the external device may include at least one of, e.g., the patient terminal 100, the medical person terminal 200, and the server 10. The medical person may receive the information through the medical person terminal 200 and may conduct a treatment by utilizing the information.

The server 10 may manage various medical information. Various types of medical information may be provided. For example, the medical information may include information regarding the patient, diagnosis results, diagnosis histories, prescriptions, checkup data, medical checkup tables, past prescription histories, past treatment histories, and other medical knowledge.

The server 10 may collect, generate, manage, store, and provide the medical information. For example, the server may receive information regarding diagnosis results or prescriptions from the medical person. As another example, the server 10 may generate a prescription or a checkup table by using a diagnosis result or diagnosis history according to a predetermined algorithm. As still another example, the server 10 may transmit medical knowledge including information regarding drugs prohibited for joint use to the doctor's terminal.

The medical person terminal 200 may receive such medical information from the server 10 and may provide the medical information to the medical person. By doing so, the medical person may conduct a further effective treatment and diagnosis.

The personal portable terminal 40 may obtain medical information from an external device and may provide the medical information to a user. The personal portable terminal 40 may include, e.g., a mobile phone or a PDA (Personal Digital Assistant). The personal portable terminal may receive a diagnosis result or an electronic prescription from at least one of, e.g., the server 10, the medical person terminal 200, and the patient terminal 100. By doing so, a user may immediately identify the diagnosis result irrespective of a place or time.

As such, the remote treatment system may share information among the constitutional elements through a communication network. The remote treatment system enables a remote treatment between a medical person and a patient, so that the medical person may conduct a further effective treatment even at a remote site, and the patient may save travel time or costs unnecessarily consumed for receiving a medical service and receive a medical treatment more quickly.

Figure 4:
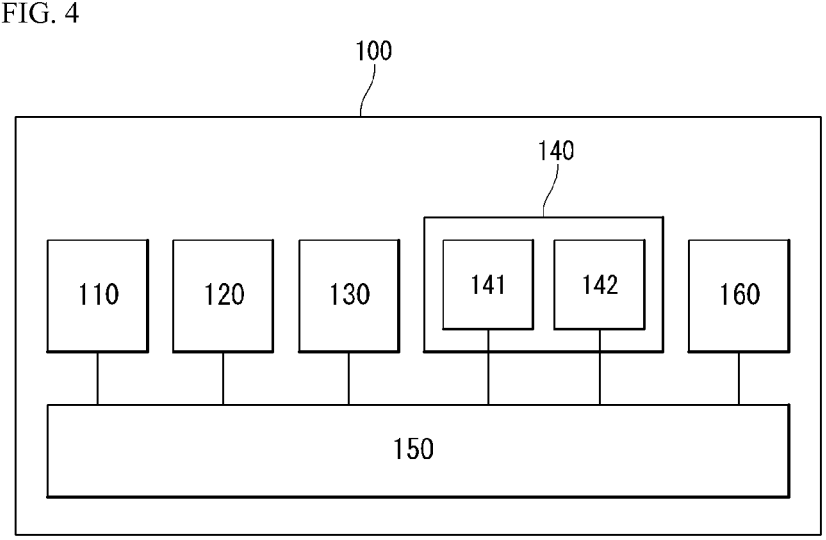
FIG. 4 is a view illustrating a configuration of a patient terminal according to an embodiment of the present invention.
Figure 5:
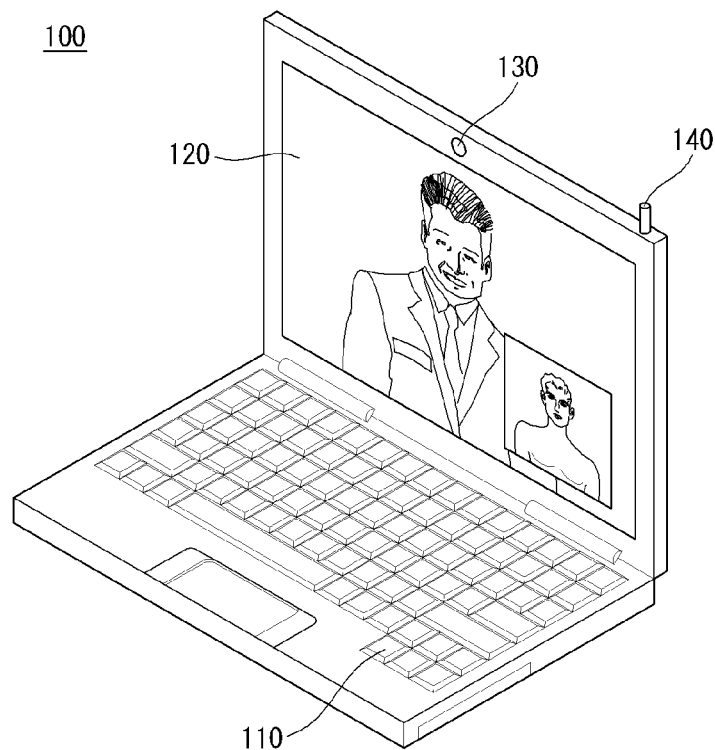
FIG. 5 is a perspective view illustrating a patient terminal according to an embodiment of the present invention.
Figure 6:
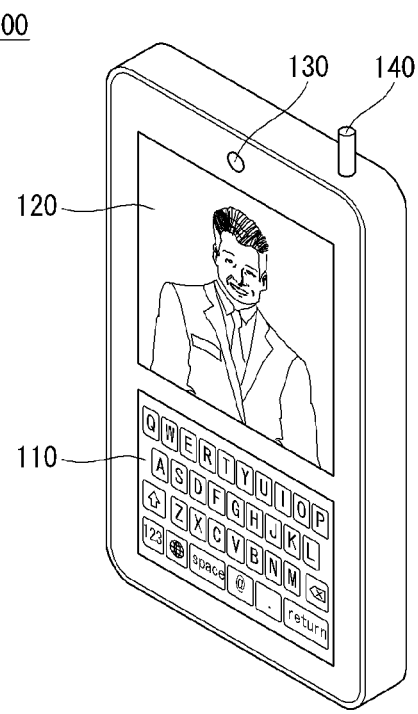
FIG. 6 is a perspective view illustrating a patient terminal according to another embodiment of the present invention.

Hereinafter, the patient terminal 100 is described in greater detail with reference to FIGS. 4, 5, and 6. FIG. 4 is a view illustrating a configuration of the patient terminal 100 according to an embodiment of the present invention. The patient terminal 100 may include at least one of an input unit 110 for receiving information from a user, an output unit 120 for outputting information to a user, a camera 130 for capturing a treatment target, a communication unit 140 for communicating with at least one of an external device and the checkup tool 30, a storage unit 160 for storing information, and a controller 150 for controlling a component of the patient terminal 100.

Hereinafter, the input unit 110, the output unit 120, the camera 130, the communication unit 140, the storage unit 160, and the controller 150 are described with reference to FIGS. 5 and 6. FIGS. 5 and 6 are perspective views illustrating the patient terminal 100 according to an embodiment of the present invention.

First, the camera 130 may capture a treatment target. The camera 130 may be included in the patient terminal 100. In contrast thereto, the camera is not included in the patient terminal 100 and may provide a captured image to the patient terminal 100. At this time, the patient terminal 100 may receive an image of the treatment target from the camera 130 through the communication unit 140.

The output unit 120 may provide information to a user. The output unit 120 may output visual, auditory, or tactile information. The output unit 120 may include at least one of a display, a speaker, and a vibration device. For example, the output unit 120 may output an image of the treatment target captured by the camera 130.

The input unit 110 may receive information from a user. The input unit 110 may include, e.g., a plurality of buttons, a touchpad, a voice recognition device, a mouse, an optical mouse, and a keyboard.

As shown in FIG. 1, the communication unit 140 may communicate with an external device. The communication may be wired communication or wireless communication through a wired/wireless communication network. The wired communication may be performed, e.g., through RS-232 or USB scheme. The wireless communication may be conducted through, e.g., Wi-Fi, Bluetooth, or ZigBee.

The communication unit 140 may include a first communication unit 141 and a second communication unit 142. The first communication unit 141 may transmit and receive medical information primarily to/from the medical person terminal 200. The second communication unit 142 may measure checkup data obtained by measuring or capturing a checkup part from the checkup tool 30. The first communication unit 141 and the second communication unit 142 may be implemented as a single physical device or as devices physically separated from each other. Further, the first communication unit 141 and the second communication unit 142 may perform communication in the same or different communication schemes.

The communication unit 140 may communicate with various devices. The communication unit 140 may communicate with at least one of, e.g., the medical person terminal 200, the server 10, a personal portable terminal, the patient terminal 100, the checkup tool 30, the Internet, and a camera. For example, the patient terminal 100 may communicate with the medical person terminal 200 to transmit an image of a treatment target and may receive the medical person's image. Here, the image may be a real-time image, and thus, the medical person and the patient may conduct a real-time remote treatment while watching each other's images.

The storage unit 160 may store information. Here, the information may be information regarding a treatment. The information regarding the treatment may be, e.g., information regarding an image of a treatment target, information regarding a checkup part, information regarding a checkup order, the name of a checkup part, the type of a checkup tool, and information regarding checkup data. The storage unit 160 may receive information from the communication unit 140, the input unit 110, the camera 130 or the controller 150 and may store the information. Further, the storage unit 160 may provide information through the communication unit 140, the output unit 120, the camera 130 and the controller 150. The storage unit 160 may be a memory. The memory may be, e.g., a flash memory, a RAM, a ROM, or a hard disk. The storage unit 160 may be embedded in the patient terminal 100 or may be detachably provided.

The controller 150 may control the other components in the patient terminal 100. Detailed description of the controller 150 is given below.

Hereinafter, a remote treatment method according to the present invention is described.

The remote treatment method according to the present invention is described by referring to the patient terminal 100 according to the present invention.

At this time, the patient terminal 100 is used for purposes of easy description of the remote treatment method according to the present invention. Accordingly, the remote treatment method according to the present invention is not limited by the patient terminal 100 according to the present invention.

The remote treatment method according to the present invention may use other devices that perform the same function as the patient terminal 100 according to the present invention.

Figure 7:
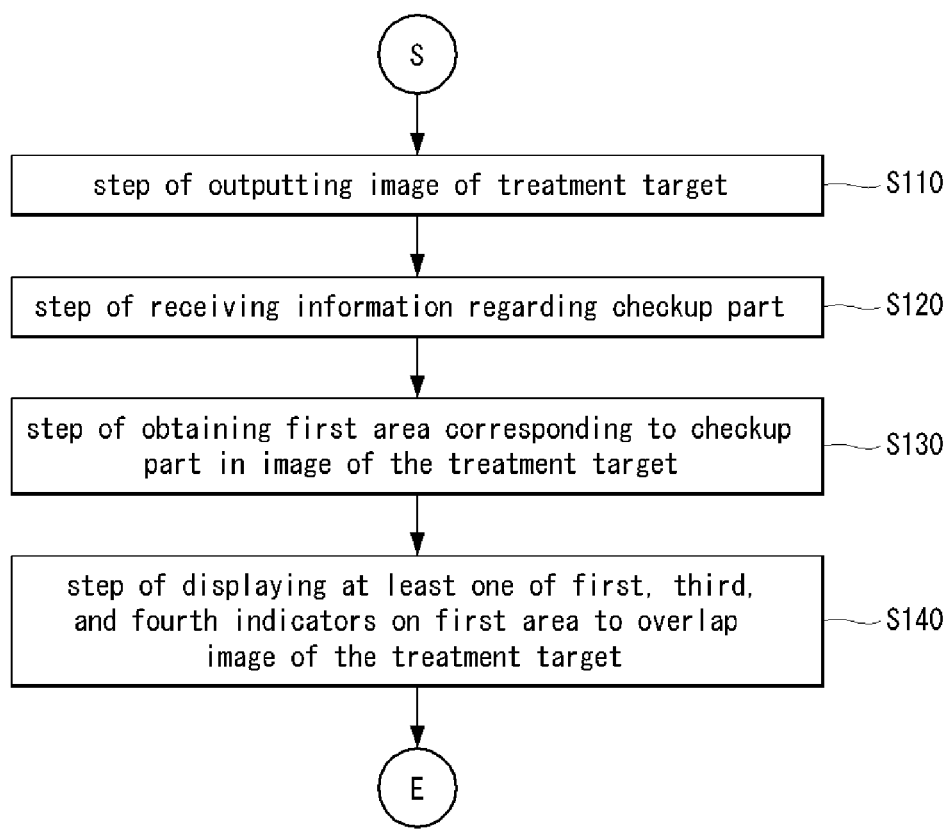
FIG. 7 is a flowchart illustrating a remote treatment method according to a first embodiment of the present invention.

Hereinafter, a remote treatment method according to a first embodiment of the present invention is described with reference to FIGS. 7, 8, and 9. FIG. 7 is a flowchart illustrating a remote treatment method according to a first embodiment of the present invention, and FIGS. 8 and 9 are views illustrating graphic user interfaces of the remote treatment method according to the first embodiment of the present invention.

The remote treatment method according to the first embodiment of the present invention may include a step of outputting an image of a treatment target (S110), a step of receiving information regarding a checkup part (S120), a step of obtaining a first area of the image of the treatment target, which corresponds to the checkup part (S130), and a step of putting at least one of a first indicator, a third indicator, and a fourth indicator on the first area to overlap the image of the treatment target (S140). Hereinafter, the steps included in the remote treatment method according to the first embodiment of the present invention are described.

First, the patient terminal 100 may output an image of a treatment target (S110). The output unit 120 of the patient terminal 100 may output the image of the treatment target. For example, the output unit 120 may include a display which may display the image of the treatment target.

As such, various images of the treatment target may be output by the output unit 120. For example, the image of the treatment target may be at least one of a real-time video of the treatment target, a recorded video, and a still image. As another example, the image of the treatment target may be a real image of the treatment target, a virtual image, or a combination image thereof.

The patient terminal 100 may obtain the image of the treatment target by various methods. For example, the patient terminal 100 may include a camera 130 that captures the treatment target, and thus, the patient terminal 100 may obtain an image of the treatment target. As another example, the patient terminal 100 may receive an image of the treatment target from an external device through the communication unit 140. As still another example, the controller 150 may generate an image of the treatment target. Specifically, the controller 150 may generate an image of the treatment target by using a virtual image of the treatment target or by combining an actual image and a virtual image of the treatment target.

Here, the patient terminal 100 has an effect of providing an image of the treatment target that may not be captured by using a virtual image. For example, the camera 130 sometimes may not capture a rear surface of the treatment target. At this time, by reflecting the rear surface of the treatment target using a virtual image, the patient terminal 100 may provide an image of the rear surface of the treatment target.

Such image of the treatment target may be stored in the storage unit 160. The storage unit 160 may store the whole or part of the image of the treatment target. For example, in case the image of the treatment target is a video, the storage unit 160 may store the video as is or may store the edited video or may store a still image of the video. The storage unit 160 may transmit the stored image to an external device through the communication unit 140.

The patient terminal 100 may receive information regarding the checkup part (S120). The patient terminal 100 may receive treatment information including information regarding the checkup part from an external device. Here, the treatment information may include a position of the checkup part, a name of the checkup part, and the type of the checkup tool 30 for the checkup part. Here, in case a plurality of checkup parts are provided, the treatment information may include an order of checkup for the plurality of checkup parts and for each checkup part. For example, the communication unit 140 may receive information regarding the checkup part from the medical person terminal 200. Here, the medical person terminal 200 may receive an input regarding the checkup part from the medical person and may generate information regarding the checkup part based on the input. Further detailed description of obtaining information regarding the checkup part by the medical person terminal 200 is given below.

Here, the information regarding the checkup part may include at least one of a position of a checkup part of a body to be treated, a name of the checkup part, and the type of the checkup tool 30 used for treatment. The information regarding a position of the checkup part may be information reflecting a specific area of an image of a treatment target. The name of the checkup part may include the name of a body part, such as a neck, a chest, and a waist. The type of the checkup tool 30 may include the type of the checkup tool 30 described above in connection with the checkup tool 30 including a thermometer or a stethoscope. For example, the information regarding the checkup part may include at least one of information reflecting a specific area corresponding to a right side of a chest of an image of a treatment target, a name reflecting the right side of a chest, and the type of the checkup tool 30 reflecting a stethoscope for auscultating the same.

The patient terminal 100 may obtain a first area corresponding to the checkup part of the image of the treatment target (S130). The controller 150 may obtain the first area corresponding to the checkup part of the image of the treatment target. In case the image of the treatment target is a video, an area corresponding to the treatment target in the output video may be shifted. Here, the controller 150 may track the first area corresponding to the checkup part of the image of the treatment target output by using an augmented reality technology. The controller 150 may track the first area by various methods. For example, the controller 150 may recognize a pattern of an area corresponding to the checkup part in the image of the treatment target. If the image of the treatment target is shifted, the controller 150 may track an area having a pattern identical to the recognized pattern. Here, the pattern may be a color tone pattern. Here, the color tone pattern may be a pattern by at least one of an RGB value and a black-and-white value. By recognizing a pattern and tracking an area corresponding to the recognized pattern in the video, the controller 150 may obtain the first area corresponding to a checkup part of an image of the treatment target.

The patient terminal 100 may put at least one of a first indicator, a third indicator, and a fourth indicator on the first area to overlap the image of the treatment target (S140). The controller 150 may control the output unit 120 so that at least one of the first, third, and fourth indicators is displayed on the first area to overlap the already output image of the treatment target.

As shown in FIG. 8, the first indicator may be an indicator that reflects the checkup part of the output image. The first indicator displayed on the image of the treatment target provides an effect of identifying which part of a body needs to be measured by the checkup tool 30 and accordingly manipulating the checkup tool 30. Such first indicator may be a mark that a user may visually recognize. As shown in FIG. 8, a position may be correctly indicated by drawing a circle or simply putting a dot on the checkup part.

Referring back to FIG. 8, the output unit 120 may further display the third and fourth indicators. The third indicator may reflect a name of the checkup part, and the fourth indicator may reflect the type of the checkup tool 30 for checking up the checkup part. For example, as shown in FIG. 8, the output unit 120 may display the first, third, and fourth indicators to overlap the image of the treatment target so that a specific area of the right side of a chest is auscultated by a stethoscope.

Here, the first, third, and fourth indicators may be displayed to overlap the image of the treatment target.

Here, the first area may track a specific area of the image of the treatment target as described above. As shown in FIG. 9, in case the treatment target is shifted, the first area is also shifted to reflect that a predetermined part of a body of the treatment target is the checkup part.

As described above, the remote treatment method according to the first embodiment of the present invention allows a user to manipulate the checkup tool 30 more easily and exactly by providing an image of a treatment target to the user by various methods and providing a checkup part, a name of the checkup part, and the type of the checkup tool 30 used for checkup to overlap the image of the treatment target.

Figure 10:
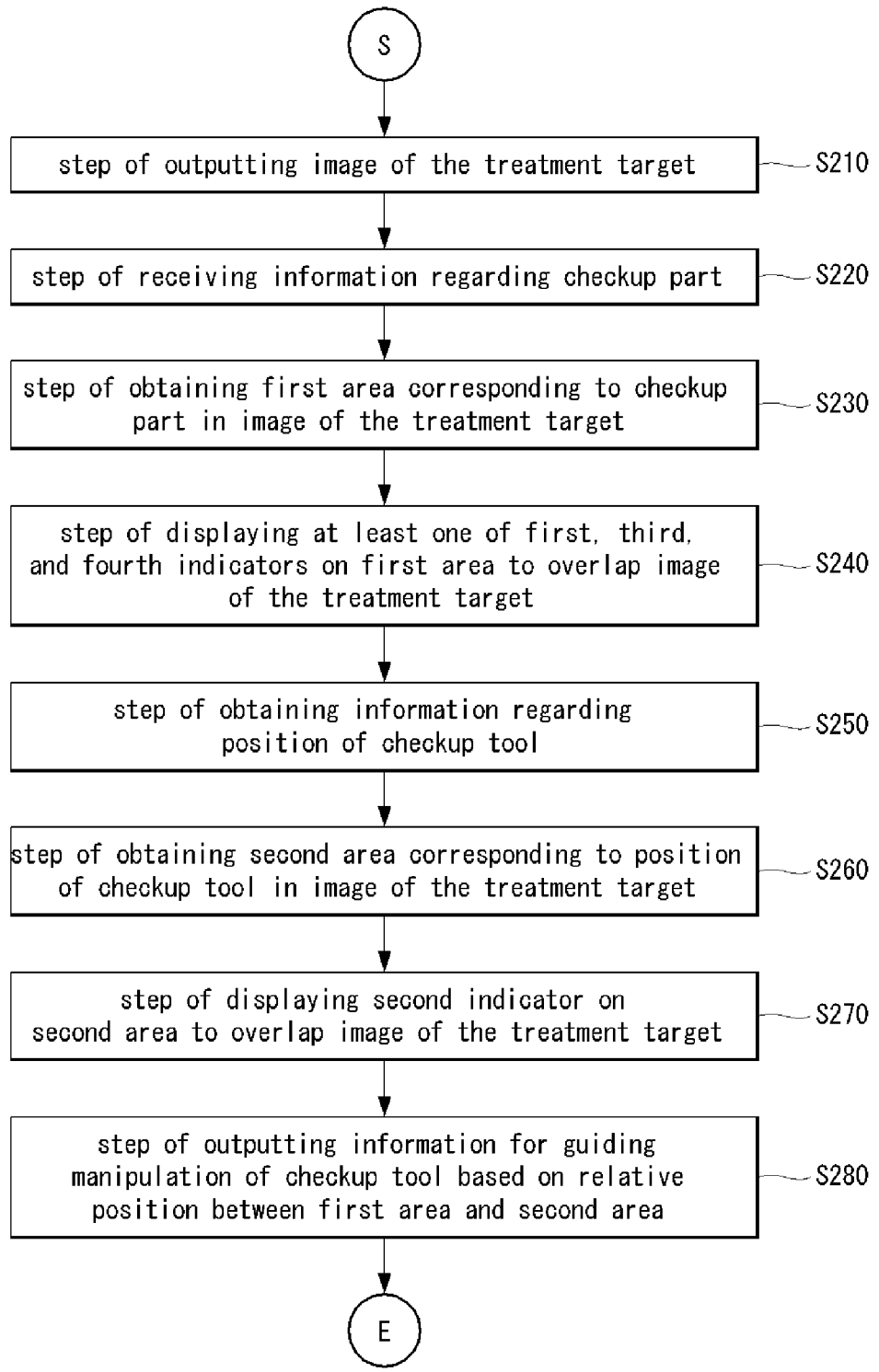
FIG. 10 is a flowchart illustrating a remote treatment method according to a second embodiment of the present invention.
Figure 11:
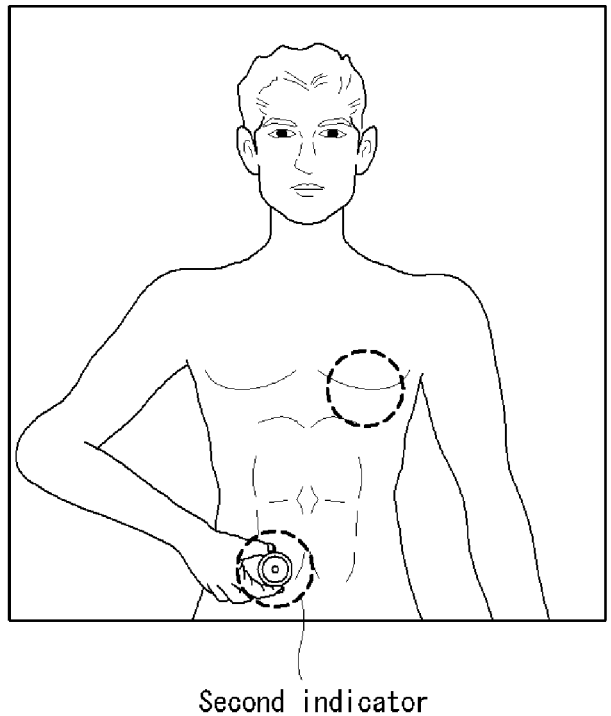
FIG. 11 is a view illustrating a first graphic user interface of a remote treatment method according to the second embodiment of the present invention.
Figure 12:
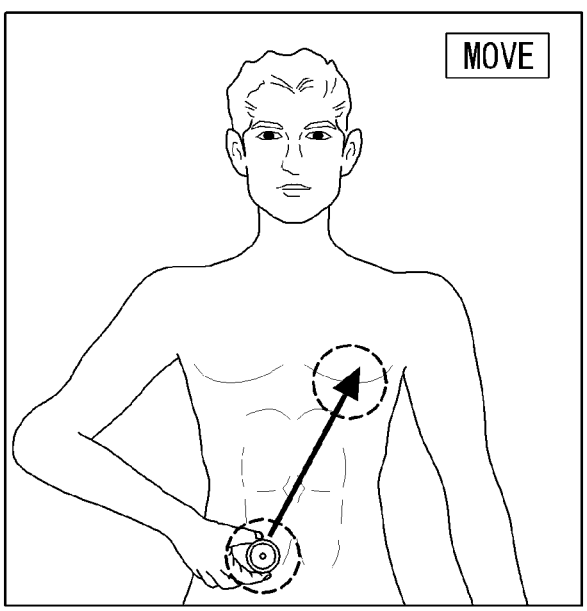
FIG. 12 is a view illustrating a first graphic user interface of the remote treatment method according to the second embodiment of the present invention.
Figure 13:
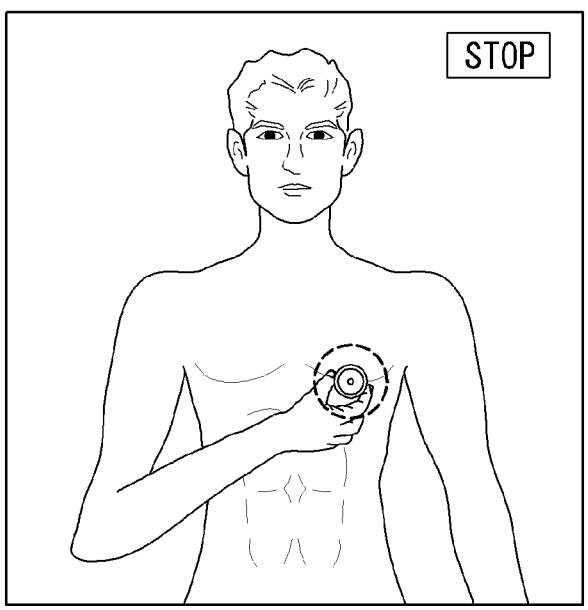
FIG. 13 is a view illustrating a first graphic user interface of the remote treatment method according to the second embodiment of the present invention.

Hereinafter, a remote treatment method according to a second embodiment of the present invention is described with reference to FIGS. 10, 11, 12, and 13. FIG. 10 is a flowchart illustrating a remote treatment method according to the second embodiment of the present invention, and FIGS. 11, 12, and 13 are views illustrating graphic user interfaces of the remote treatment method according to the second embodiment of the present invention.

The remote treatment method according to the second embodiment of the present invention may include a step of outputting an image of a treatment target (S210), a step of receiving information regarding a checkup part (S220), a step of obtaining a first area corresponding to the checkup part in the image of the treatment target (S230), a step of displaying a first indicator on the first area to overlap the image of the treatment target (S240), a step of receiving information for guiding a manipulation of the checkup tool 30 or obtaining information regarding a position of the checkup tool 30 (S250), a step of obtaining a second area corresponding to the position of the checkup tool 30 in the image of the treatment target (S260), a step of displaying a second indicator on the second area to overlap the image of the treatment target (S270), and a step of outputting the information for guiding the manipulation of the checkup tool 30. Hereinafter, the steps included in the remote treatment method according to the second embodiment of the present invention are described.

First, the step of outputting the image of the treatment target (S210), the step of receiving the information regarding the checkup part (S220), the step of obtaining the first area corresponding to the checkup part in the image of the treatment target (S230), and the step of displaying the first indicator on the first area to overlap the image of the treatment target may be the same as those described above in the remote treatment method according to the first embodiment of the present invention.

The patient terminal 100 may obtain information regarding a position of the checkup tool 30 or may receive information for guiding a manipulation of the checkup tool 30 (S250). For example, the patient terminal 100 may include a camera 130 that may capture the treatment target. At this time, an image of the checkup tool 30 may be included in the captured image of the treatment target. The controller 150 may determine a position of the checkup tool 30 based on the image of the treatment target including the image of the checkup tool 30. As another example, the communication unit 140 may receive information regarding the position of the checkup tool 30 from the checkup tool 30. By doing so, the patient terminal 100 may obtain the information regarding the position of the checkup tool 30. As still another example, the patient terminal 100 may receive information for guiding a manipulation of the checkup tool 30 from an external device. here, the external device may include the medical person terminal 200. As a specific example, the medical person terminal 200 may receive information for guiding a manipulation of the checkup tool 30 from a doctor and may transmit the information to the patient terminal 100. By doing so, the patient terminal 100 may obtain the information regarding the position of the checkup tool 30 or may receive the information for guiding the manipulation of the checkup tool 30.

The patient terminal 100 may obtain a second area corresponding to a position of the checkup tool 30 in the image of the treatment target (S260). The controller 150 may obtain the second area corresponding to the position of the checkup tool 30 in the image of the treatment target based on the information regarding the position of the checkup tool 30. The controller 150 may obtain the second area by recognizing the checkup tool 30 captured together with the image of the treatment target and tracing the second area where the checkup tool 30 is positioned in the image of the treatment target by using an augmented reality technology by the same method as the step of obtaining the first area as described above. Or, the controller 150 may obtain the second area where the checkup tool 30 is positioned based on the information regarding the position of the treatment target.

The patient terminal 100 may display a second indicator on the second area to overlap the image of the treatment target (S270). The controller 150 may control the output unit 120 so that the second indicator is displayed on the obtained second area. Such second indicator may reflect the checkup tool 30. As described in FIG. 11, the controller 150 may control the output unit 120 so that the second indicator is displayed on the second area where a stethoscope is positioned in the image of the treatment target in which the treatment target and the stethoscope are captured together. By doing so, the patient terminal 100 may provide the information regarding the position of the checkup tool 30 to a user. Such patient terminal 100 provides an effect of allowing a user to receive signals respectively reflecting a checkup part and the checkup tool 30 on the image of the treatment target and to thereby easily manipulate the checkup tool 30.

The patient terminal 100 may output the information for guiding the manipulation of the checkup tool 30 (S280). The controller 150 may control the output unit 120 to output the information for guiding the manipulation of the checkup tool 30. The controller 150 may perform control so that the information for guiding the manipulation of the checkup tool 30 is generated by various methods and output by the output unit 120.

The controller 150 may control the output unit 120 to output the information for guiding the manipulation of the checkup tool 30 based on a relative position between the first and second areas. For example, the controller 150 may generate the information for guiding the manipulation of the checkup tool 30 based on whether the first and second areas are placed at the same position, for example, where the first and second areas are identical to each other. Or, the controller 150 may generate the information for guiding the manipulation of the checkup tool 30 based on whether part of the second area is included in the first area. At this time, the information for guiding the manipulation of the checkup tool 30 may be output as an alarm signal through the output unit 120. Such alarm signal may include at least one of visual, auditory, and tactile signals.

For example, when the first and second areas are inconsistent with each other, the controller 150 may generate information for indicating a shift of the checkup tool 30 as shown in FIG. 12. Here, the information for indicating the shift may include information including at least one of a shift distance and a shift direction. As shown in FIG. 12, the output unit 120 may output a signal indicating a direction and distance of the first area with respect to the second area on the image of the treatment target. At this time, a separate sign indicating the shift may be output. Further, the controller 150 may control the output unit 120 to output a sound signal whose volume is determined based on a relative distance between the first and second areas. For example, the output unit 120 may output a sound signal with a low volume when the first and second areas are far away from each other, and may output a higher volume of sound signal as the first and second areas become closer to each other. Similarly, the output unit 120 may output a vibration according to a relative distance between the first and second areas.

As another example, the controller 150 may control the output unit 120 to output information indicating a pause of the checkup tool 30 as shown in FIG. 13 when the first and second areas are consistent with each other. For example, the output unit 120 may output a sign indicating a pause of the checkup tool 30 on the image of the treatment target. Further, the output unit 120 may display separate information indicating a pause of the checkup tool 30 on a space other than the image of the treatment target. Or, the output unit 120 may output at least one of a voice message and a vibration message indicating when the first area is consistent with the second area.

The controller 150 may control the output unit 120 to output the information for guiding the manipulation of the checkup tool 30 based on the obtained information regarding the position of the checkup tool 30. For example, the controller 150 may determine a relative position between a checkup part and the checkup tool 30 based on the information regarding the position of the checkup tool 30. For example, when the position of the checkup tool 30 is consistent with the checkup part, the output unit 120 may output a signal indicating a pause of the checkup tool 30. On the contrary, when the position of the checkup tool 30 is spaced apart from the checkup part, the output unit 120 may output a signal indicating at least one of a shift direction and a shift distance for manipulation of the checkup tool 30. Such signals may include a voice, a vibration, and an image signal as described above.

Or, the controller 150 may receive the information for guiding the manipulation of the checkup tool 30 from an external device, and based on the received information, may control the output unit 120 to output information. As described above, the output unit 120 may output an image signal, a voice signal, and a vibration signal as the information for guiding the manipulation of the checkup tool 30.

Here, the information for guiding the manipulation of the checkup tool 30 may include information regarding at least one of whether the shift of the checkup tool 30 is stopped, a shift direction, and a shift distance.

As such, the patient terminal 100 may guide a user regarding a manipulation of the checkup tool 30 by outputting the information for guiding the manipulation of the checkup tool 30, a checkup part, and a position of the checkup tool 30 to the user. The patient terminal 100 provides an effect of allowing the user to easily and correctly manipulate the checkup tool 30.

Figure 14:
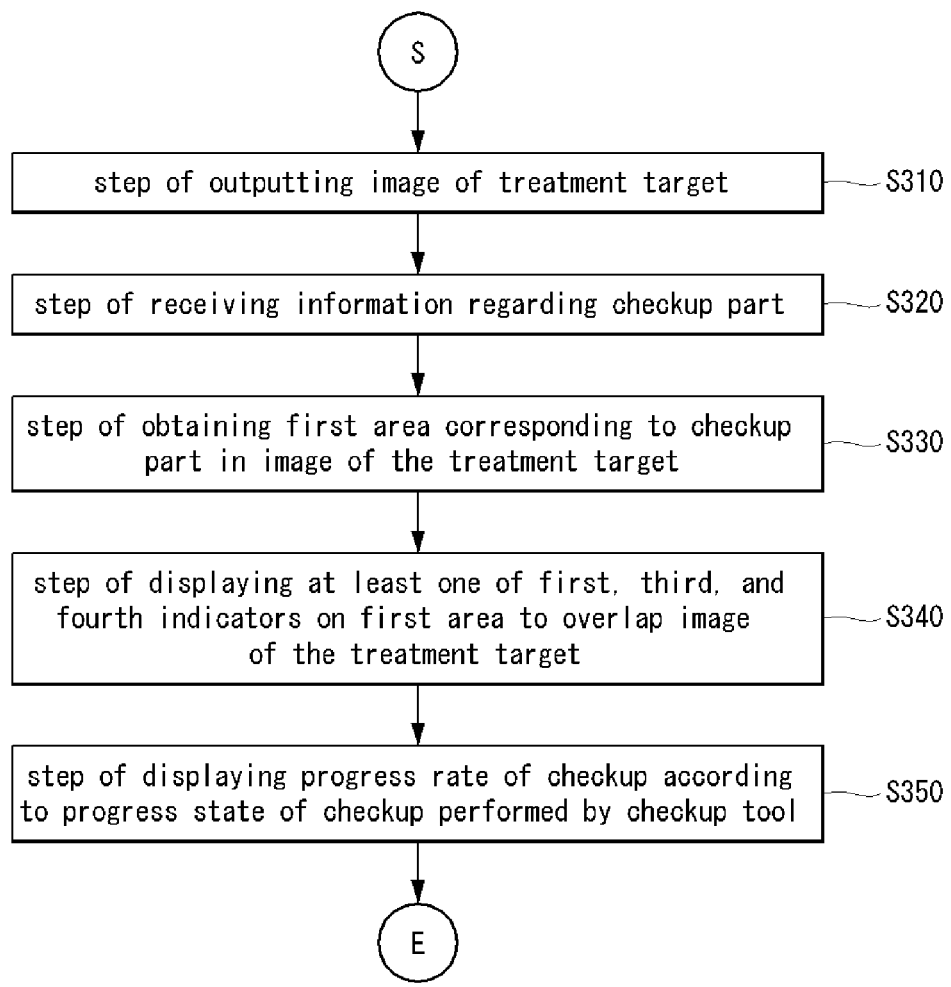
FIG. 14 is a flowchart illustrating a remote treatment method according to a third embodiment of the present invention.
Figure 15:
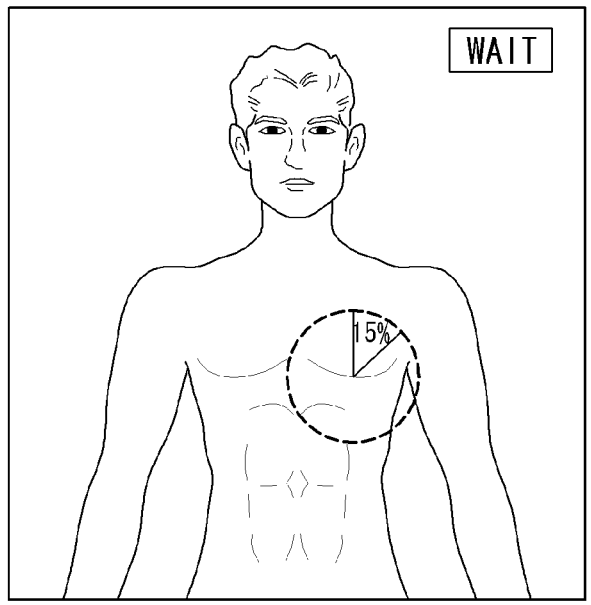
FIG. 15 is a view illustrating a first graphic user interface of the remote treatment method according to the third embodiment of the present invention.
Figure 16:
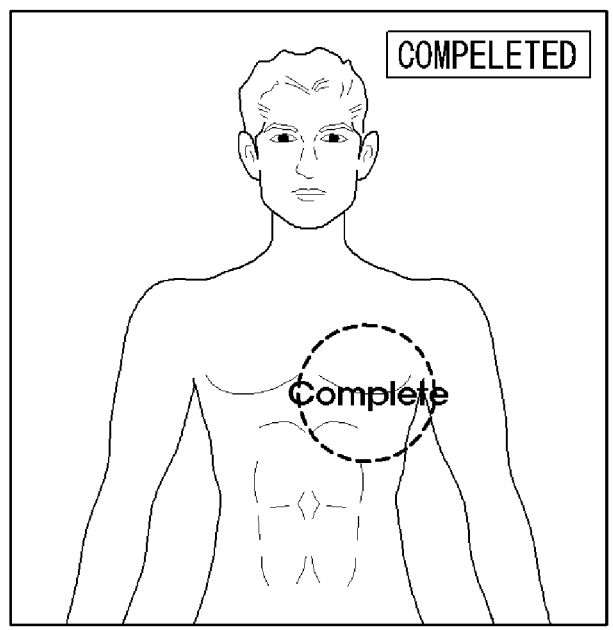
FIG. 16 is a view illustrating a second graphic user interface of the remote treatment method according to the third embodiment of the present invention.

Hereinafter, a remote treatment method according to a third embodiment of the present invention is described with reference to FIGS. 14, 15, and 16. FIG. 1 is a flowchart illustrating a remote treatment method according to the third embodiment of the present invention, and FIGS. 15 and 16 are views illustrating graphic user interfaces of the remote treatment method according to the third embodiment of the present invention.

The remote treatment method according to the third embodiment of the present invention may include a step of outputting an image of a treatment target (S310), a step of receiving information regarding a checkup part (S320), a step of obtaining a first area corresponding to the checkup part in the image of the treatment target (S330), a step of displaying a first indicator on the first area to overlap the image of the treatment target (S340), and a step of displaying a checkup progress rate based on a degree at which the checkup is in progress by the checkup tool 30. Hereinafter, the steps included in the remote treatment method according to the third embodiment of the present invention are described.

First, the step of outputting the image of the treatment target (S310), the step of receiving the information regarding the checkup part (S320), the step of obtaining the first area corresponding to the checkup part in the image of the treatment target (S330), and the step of displaying the first information on the first area to overlap the image of the treatment target may be identical to those described above in connection with the remote treatment method according to the first embodiment of the present invention.

The patient terminal 100 may display a checkup progress rate based on the degree at which the checkup is in progress by the checkup tool 30 (S350). The controller 150 may obtain the checkup progress rate and control the output unit 120 to display the checkup progress rate. The controller 150 may receive the checkup progress rate from the checkup tool 30. Or, the controller 150 may obtain checkup data for the checkup part from the checkup tool 30 and may determine the checkup progress rate based on the obtained checkup data. Or, the communication unit 140 may receive information regarding a checkup progress rate from an external device, e.g., the medical person terminal 200, and based on this, the controller 150 may control the output unit 120 to output the checkup progress rate.

As shown in FIG. 15, the output unit 120 may display the checkup progress rate on the image of the treatment target and the degree at which the checkup is in progress. At this time, the output unit 120 may display the checkup progress rate to overlap the first area. The output unit 120 may display the checkup progress rate by using a figure or numeral. Or, the output unit 120 may output a voice signal or vibration signal as the checkup progress rate. For example, the output unit 120 may output a voice notification message regarding how much the checkup is in progress.

Meanwhile, the controller 150 may yield a remaining checkup time based on the checkup progress rate and control the output unit 120 to output the remaining checkup time. For example, if the checkup has been 50% done one minute after the checkup tool 30 started the checkup, the output unit 120 may output an image or voice signal reflecting that the checkup has one minute left.

As shown in FIG. 16, when the checkup is completed, the output unit 120 may output information indicating that the checkup has been done. For example, the output unit 120 may display a figure or text message to overlap the first area to indicate that the checkup has been complete. Or, the server 10 may delete the first indicator from the first area when the checkup is completed.

As such, the patient terminal 100 may provide a user with at least one of information reflecting how much a checkup has been done, how further the checkup should be done, how long the checkup takes to be done, and whether the checkup has been complete. By doing so, the user may manipulate the checkup tool 30 more easily and correctly when using the patient terminal 100 and may be aware of how much the manipulation of the checkup tool 30 has been done.

Figure 17:
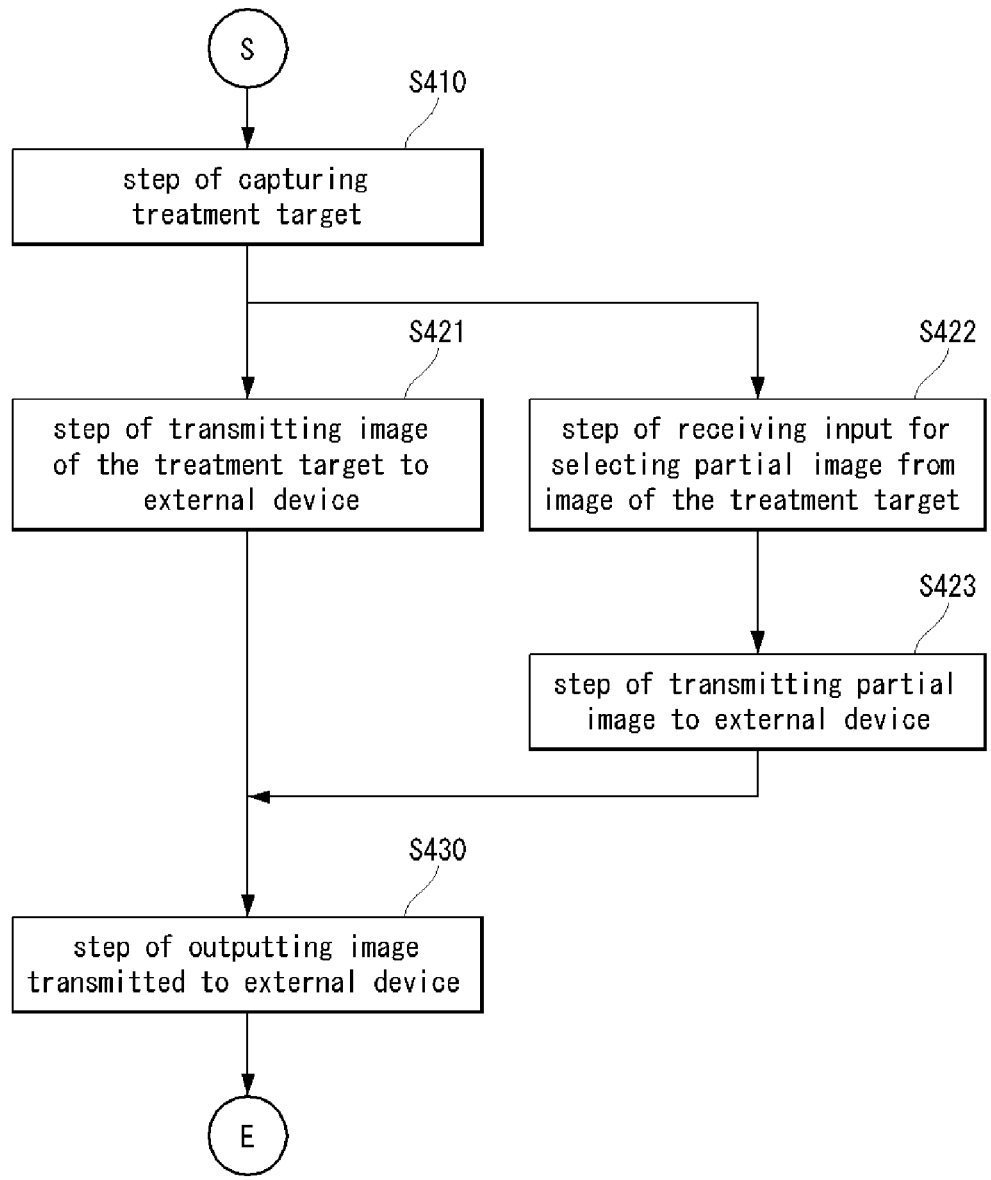
FIG. 17 is a flowchart illustrating a remote treatment method according to a fourth embodiment of the present invention.
Figure 18:
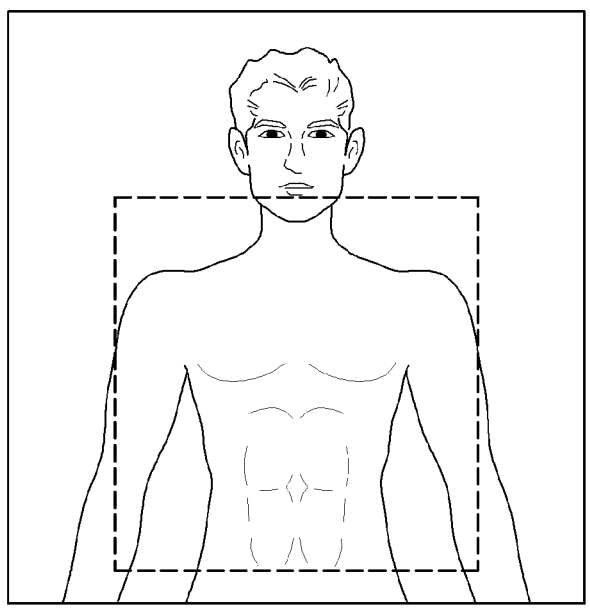
FIG. 18 is a view illustrating a first graphic user interface of the remote treatment method according to the fourth embodiment of the present invention.
Figure 19:
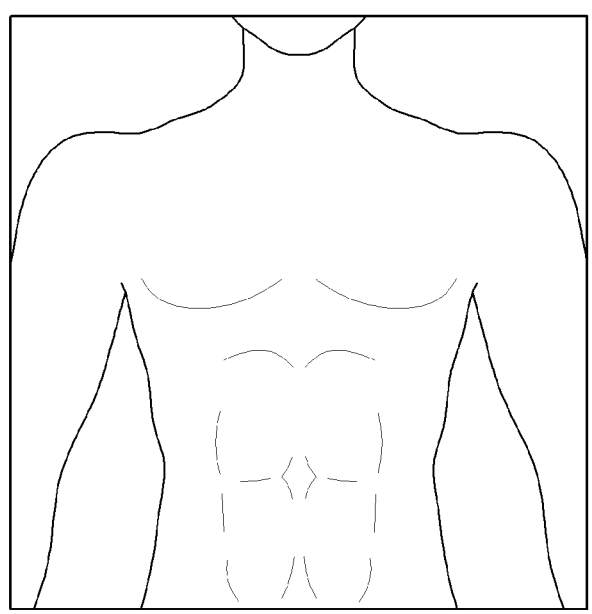
FIG. 19 is a view illustrating a second graphic user interface of the remote treatment method according to the fourth embodiment of the present invention.

Hereinafter, a remote treatment method according to a fourth embodiment of the present invention is described with reference to FIGS. 17, 18, and 19. FIG. 17 is a flowchart illustrating the remote treatment method according to the fourth embodiment of the present invention, and FIGS. 18 and 19 are views illustrating graphic user interfaces of the remote treatment method according to the fourth embodiment of the present invention.

The remote treatment method according to the fourth embodiment of the present invention may include a step of capturing a treatment target (S410), a step of transmitting an image of the treatment target to an external device (S421), a step of receiving an input for selecting a part of the image of the treatment target (S422), a step of transmitting the partial image to the external device (S423), and a step of outputting the image transmitted to the external device. Here, the remote treatment method according to the fourth embodiment of the present invention may selectively include a step of transmitting the image of the treatment target to the external device (S421), and steps of receiving an input for selecting a part of the image of the treatment target (S422) and transmitting the partial image to the external device (S423). Hereinafter, the steps included in the remote treatment method according to the fourth embodiment of the present invention are described.

The patient terminal 100 may capture a treatment target (S410). The patient terminal 100 may include a camera 130 that may capture the treatment target. Or, the patient terminal 100 may obtain an image of the treatment target from a separate imaging device that is not included in the patient terminal 100.

The patient terminal 100 may transmit the image of the treatment target to an external device (S421). The communication unit 140 may treatment the captured image of the treatment target to the external device. The transmission may be performed through a communication network. Here, the external device may include the medical person terminal 200.

The external device may output the transmitted image (S430). Here, the external device may be the medical person terminal 200. The medical person terminal 200 may provide the image of the treatment target to a medical person. The medical person may receive the image and may have a real-time video call with a patient to thereby perform a remote treatment. Further, the medical person may perform a clinical diagnosis or determine a checkup part by viewing the output image of the treatment target. The medical person terminal 200 may receive information regarding the checkup part from the medical person and may transmit the received information to the patient terminal 100. By doing so, the same effect as that obtained by a face-to-face treatment may be achieved between the medical person and the patient who reside at remote sites.

On the contrary, the patient terminal 100 may transmit a partial image only rather than immediately transmitting the whole image of the treatment target.

First, the patient terminal 100 may capture the treatment target and then may receive an input for selecting a partial image of the image of the treatment target (S422). The input unit 110 may receive the input for selecting part of the image of the treatment target which has been captured by a user. For example, the image of the treatment target is output to the output unit 120 of the patient terminal 100, and the user may select part of the image. The user may select the part of the image of the treatment target by using a mouse or touch screen. The medical person terminal 200 may thus receive the selected part of the whole image of the treatment target from the user.

The partial image may include an image of a partial area of the whole image of the treatment target as shown in FIG. 18. Or, the partial image may include at least one of a specific still image and an image including some frames corresponding to a predetermined section among all the frames in the image of the treatment target, which is a video.

The patient terminal 100 may transmit only the selected partial image of the image of the treatment target (S423). Accordingly, the external device, e.g., the medical person terminal 200, may output not the entire image of the treatment target but the partial image as shown in FIG. 19.

As such, the patient terminal 100 may transmit not the entire image of the treatment target but the partial image to the medical person terminal 200, and the medical person terminal 200 may provide only the partial image. The patient terminal 100 may provide only an image necessary for treatment which is other than a part which the user does not want to be viewed by the medical person, and the medical person terminal 200 may provide the medical person with only the image necessary for treatment, so that the patient's privacy may be protected. For example, a patient with a venereal disease or who feels shame from the treatment may select only a body part except for his/her face from the image of the treatment target, thereby protecting his/her privacy.

Figure 20:
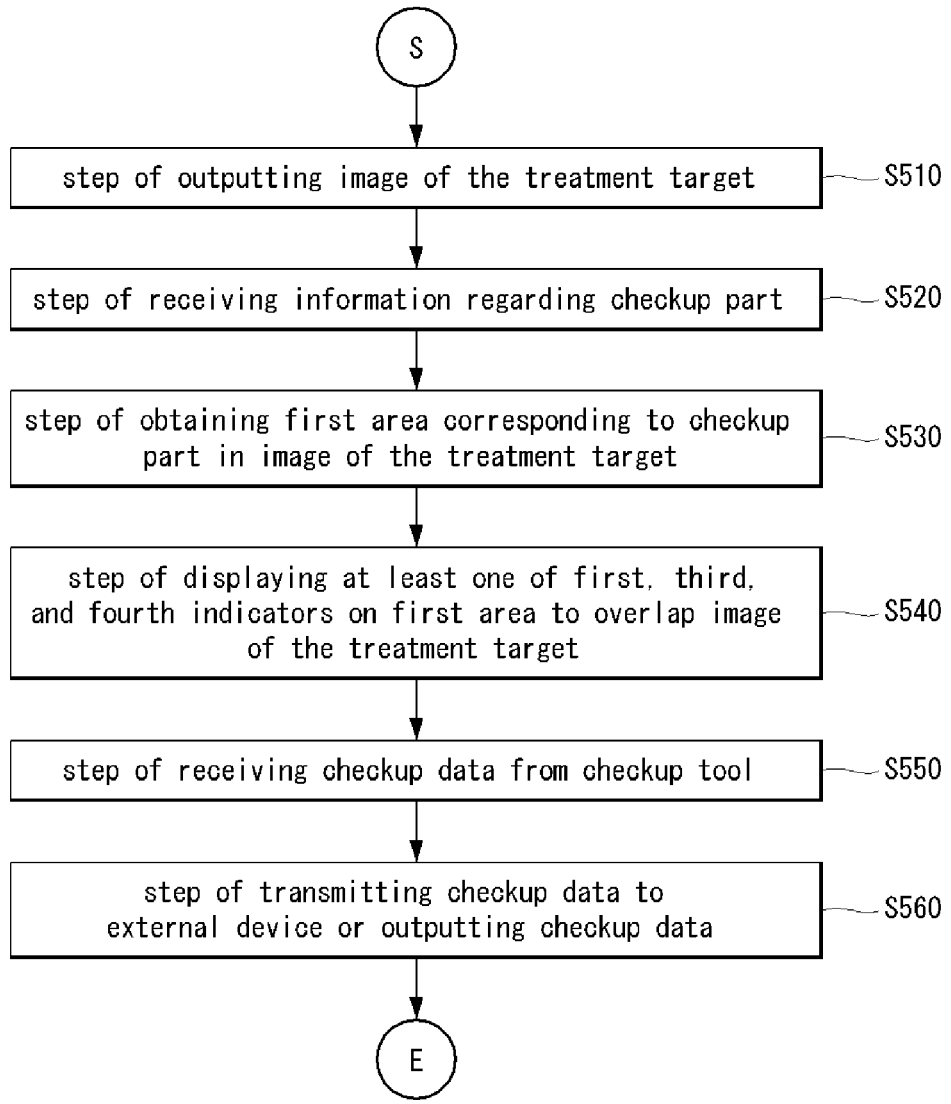
FIG. 20 is a flowchart illustrating a remote treatment method according to a fifth embodiment of the present invention.
Figure 21:
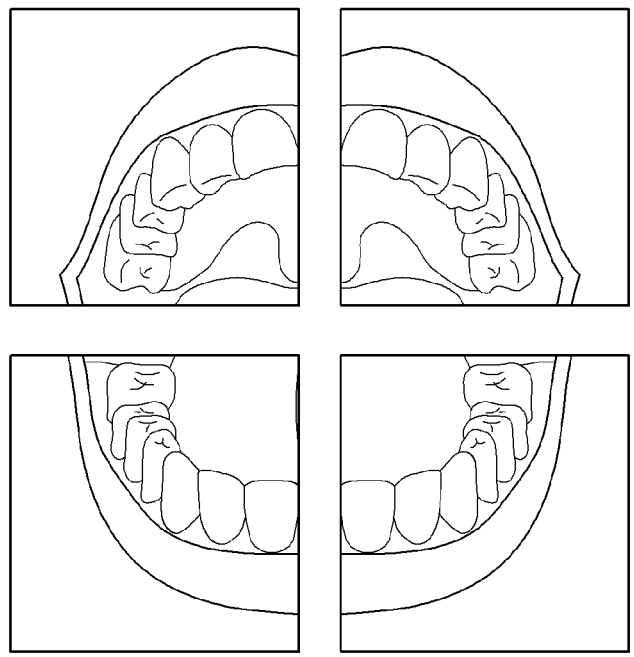
FIG. 21 is a view illustrating a partial image of a checkup part of the remote treatment method according to the fifth embodiment of the present invention.
Figure 22:
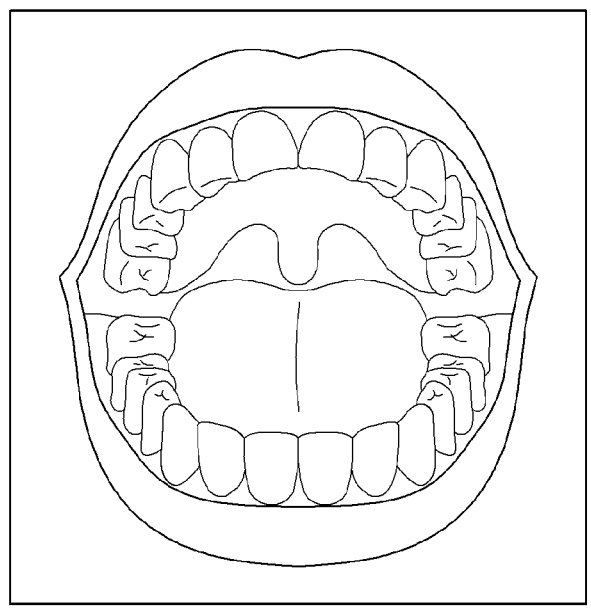
FIG. 22 is a view illustrating an entire image of a checkup part of the remote treatment method according to the fifth embodiment of the present invention.
Figure 23:
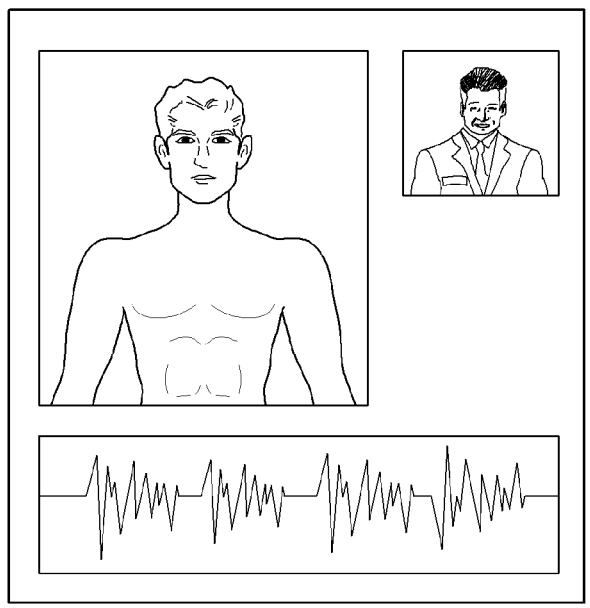
FIG. 23 is a view illustrating a graphic user interface of the remote treatment method according to the fifth embodiment of the present invention.

Hereinafter, a remote treatment method according to a fifth embodiment of the present invention is described with reference to FIGS. 20, 21, 22, and 23. FIG. 20 is a flowchart illustrating the remote treatment method according to the fifth embodiment of the present invention, FIG. 21 is a view illustrating a partial image of a checkup part in the remote treatment method according to the fifth embodiment of the present invention, and FIG. 22 is a view illustrating an entire image of a checkup part in the remote treatment method according to the fifth embodiment of the present invention. FIG. 23 is a view illustrating a graphic user interface in the remote treatment method according to the fifth embodiment of the present invention.

The remote treatment method according to the fifth embodiment of the present invention may include a step of outputting an image of a treatment target (S510), a step of receiving information regarding a checkup part (S520), a step of obtaining a first area corresponding to the checkup part in the image of the treatment target (S530), a step of displaying a first indicator on the first area to overlap the image of the treatment target (S540), a step of receiving checkup data from the checkup tool 30 (S550), and a step of transmitting the checkup data to an external device or outputting the checkup data (S560). Hereinafter, the steps included in the remote treatment method according to the fifth embodiment of the present invention are described.

First, the step of outputting the image of the treatment target (S51), the step of receiving the information regarding the checkup part (S520), the step of obtaining the first area corresponding to the checkup part in the image of the treatment target (S530), and the step of displaying the first indicator on the first area to overlap the image of the treatment target (S540) may be the same as those described above in connection with the remote treatment method according to the first embodiment of the present invention.

The patient terminal 100 may receive checkup data from the checkup tool 30 (S550). For example, the communication unit 140 may receive the checkup data from the checkup tool 30. Here, the checkup data may include at least one of bio-information measured from the checkup part and an affected part image obtained by capturing the checkup part. For example, the checkup tool 30 may include a stethoscope that may sense a stethoscopic sound from the checkup part while contacting the checkup part. The stethoscopic sound sensed by the stethoscope may be transmitted to the patient terminal 100. As another example, the checkup tool 30 may include a microscope that may capture a precision image of the checkup part. The affected part image captured by the microscope may be transmitted to the patient terminal 100. The patient terminal 100 may receive checkup data from the checkup tool 30.

Here, the controller 150 may receive the checkup data from the checkup tool 30 and may process the checkup part by using the same. For example, the controller 150 may obtain a stethoscopic sound from a stethoscope through the communication unit 140 and may remove a noise signal from the obtained stethoscopic sound or adjust the volume of the stethoscopic sound. By doing so, the doctor may be provided with noise-removed stethoscopic sound with a reinforced part necessary for a clinical determination, thereby providing a more precise treatment. As another example, a microscope may capture a plurality of partial images of the checkup part and the controller 150 may receive the plurality of partial images through the communication unit 140. The controller 150 may combine the received partial images to thereby generate a whole image. Specifically, for example, as shown in FIG. 21, the microscope may capture a plurality of partial images of an oral cavity. The controller 150 may combine the plurality of partial images to thereby generate a whole image for the oral cavity as shown in FIG. 22.

The patient terminal 100 may transmit checkup data to an external device or output the checkup data (S560).

The communication unit 140 may transmit the checkup data transmitted from the checkup tool 30 or processed checkup data of the checkup data to the medical person terminal 200. The medical person terminal 200 may receive the checkup data and provide the received checkup data to the medical person, thus assisting in the medical person's clinical determination.

Or, the patient terminal 100 may output the checkup data as shown in FIG. 23. The controller 150 may control the output unit 120 to output the checkup data. For example, as shown in FIG. 23, the output unit 120 may output an image or sound as a pattern of a stethoscopic image received from a stethoscope.

As such, the patient terminal 100 and the medical person terminal 200 may receive and output the checkup data, so that the patient or medical person may be provided with the checkup data. By using the patient terminal 100 and the medical person terminal 200, the patient and the medical person may share exact checkup data even when they stay apart from each other at remote sites, so that more effective remote treatment may be achieved.

Figure 24:
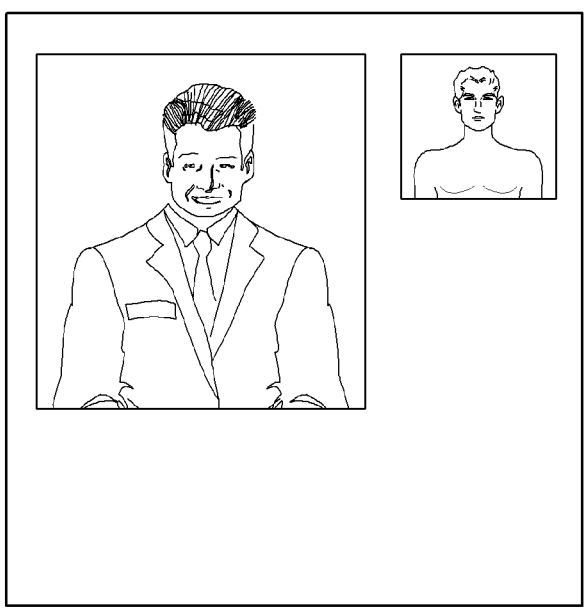
FIG. 24 is a view illustrating a first graphic user interface of a remote treatment method according to a sixth embodiment of the present invention.
Figure 25:
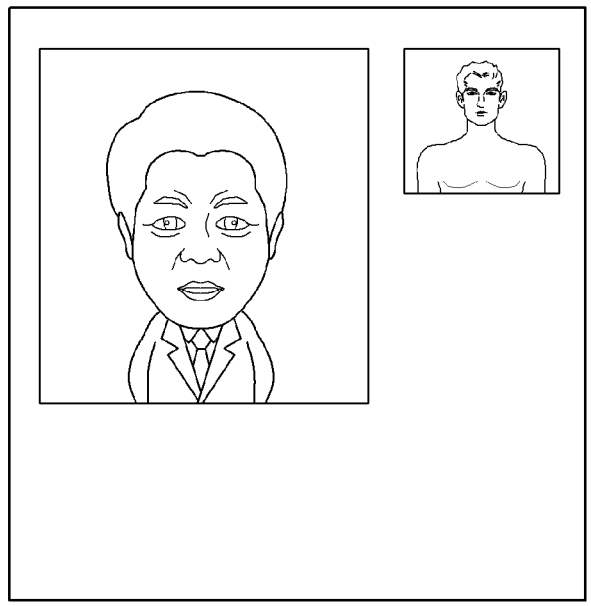
FIG. 25 is a view illustrating a second graphic user interface of the remote treatment method according to the sixth embodiment of the present invention.

Hereinafter, a remote treatment method according to a sixth embodiment of the present invention is described with reference to FIGS. 24 and 25. FIGS. 24 and 25 are views illustrating graphic user interfaces of the remote treatment method according to the sixth embodiment of the present invention.

The remote treatment method according to the sixth embodiment of the present invention may include a step of receiving an image of a medical person (S610), a step of outputting the image of the medical person (S620), a step of outputting an image of a treatment target (S630), a step of receiving information regarding a checkup part (S640), a step of obtaining a first area corresponding to the checkup part in the image of the treatment target (S650), and a step of displaying a first indicator on the first area to overlap the image of the treatment target (S660). Hereinafter, the steps included in the remote treatment method according to the sixth embodiment of the present invention are described.

The patient terminal 100 may receive the image of the medical person (S610). The communication unit 140 may receive the image of the medical person from the medical person terminal 200. Here, the medical person terminal 200 may include a camera 130 that may capture the image of the medical person. Or, the medical person terminal 200 may receive an image captured by a separate camera which is not included in the medical person terminal 200. The communication unit 140 may receive the image of the medical person from the medical person terminal 200.

The patient terminal 100 may output the image of the medical person (S620). Here, the medical person's image may be the same or different from an image received by the communication unit 140 from the medical person terminal 200. As shown in FIG. 24, the output unit 120 may output an actual image of the medical person. By doing so, a user may receive a remote treatment while viewing the medical person's image.

Or, the output unit 120 may output a virtual image of the medical person or a combined image of an actual image and a virtual image of the medical person. For example, as shown in FIG. 25, the medical person's image may include a replacement image, such as a character, a predetermined model, or an avatar. By doing so, a patient may receive a treatment without directly facing the medical person. Thus, at least one of the medical person and the patient may protect his privacy.

The step of outputting the image of the treatment target (S630), the step of receiving the information regarding the checkup part (S640), the step of obtaining the first area corresponding to the checkup part in the image of the treatment target (S650), and the step of displaying the first indicator on the first area to overlap the image of the treatment target (S660) may be the same as those described above in connection with the remote treatment method according to the first embodiment of the present invention.

Figure 26:
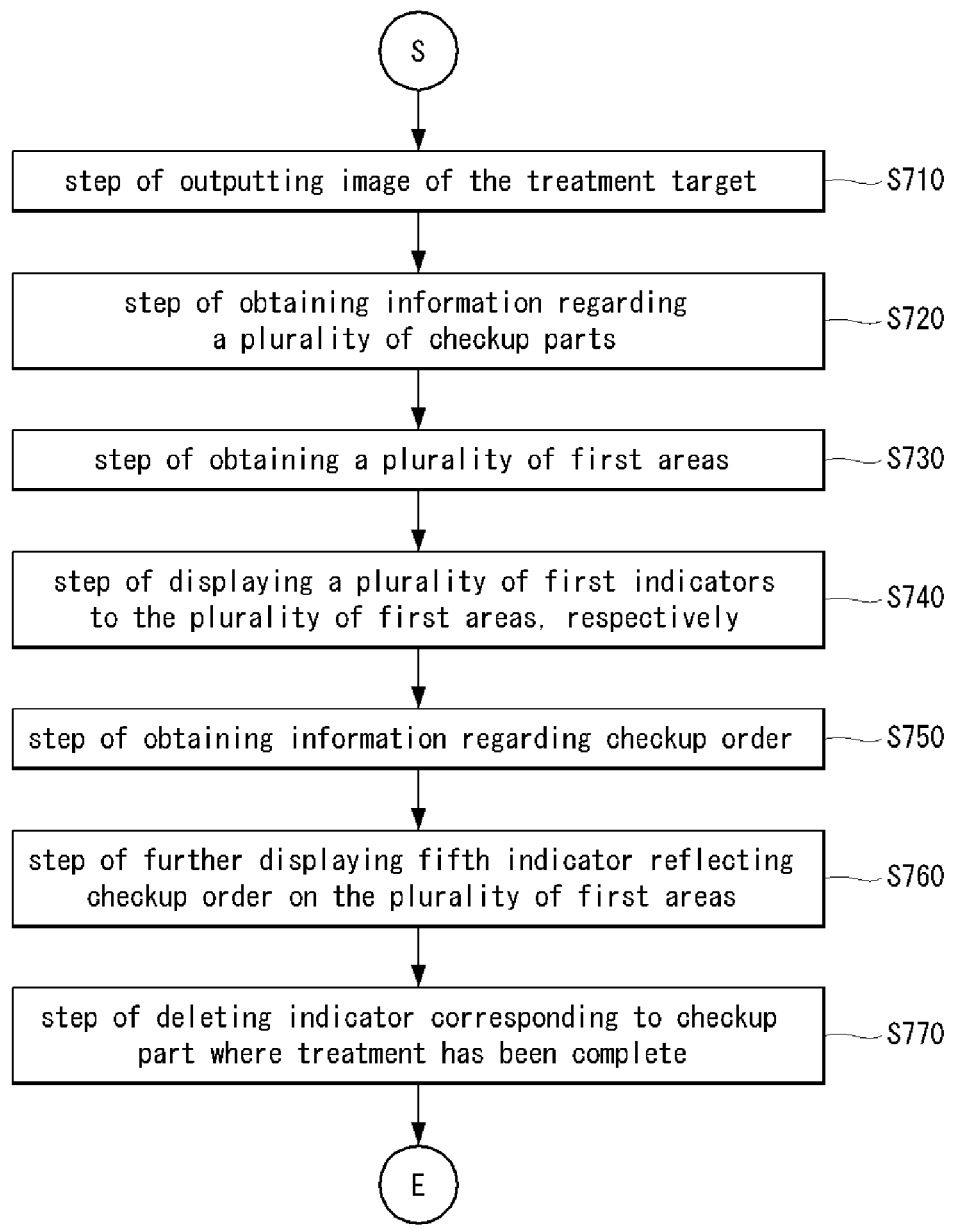
FIG. 26 is a flowchart illustrating a remote treatment method according to a seventh embodiment of the present invention.
Figure 27:
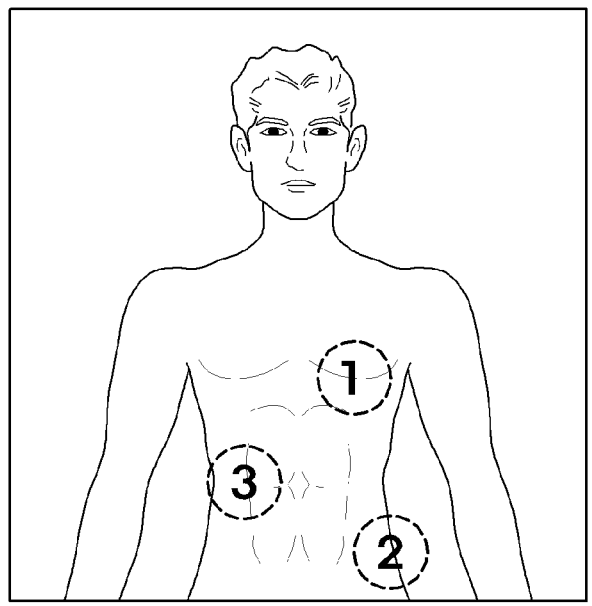
FIG. 27 is a view illustrating a first graphic user interface of the remote treatment method according to the seventh embodiment of the present invention.
Figure 28:
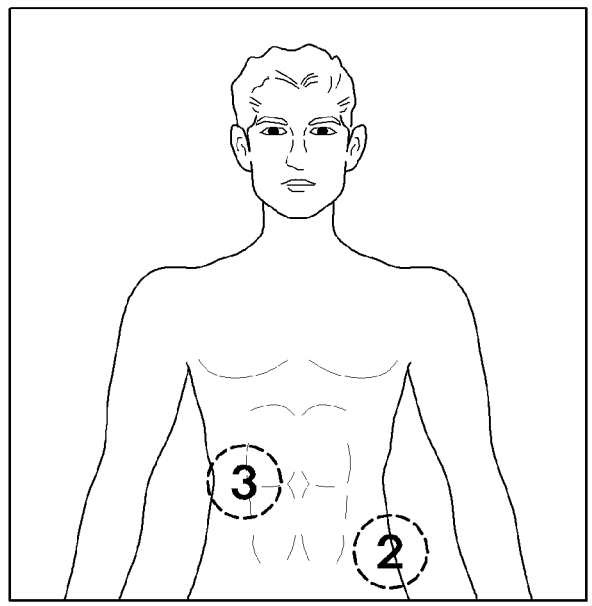
FIG. 28 is a view illustrating a second graphic user interface of the remote treatment method according to the seventh embodiment of the present invention.
Figure 29:
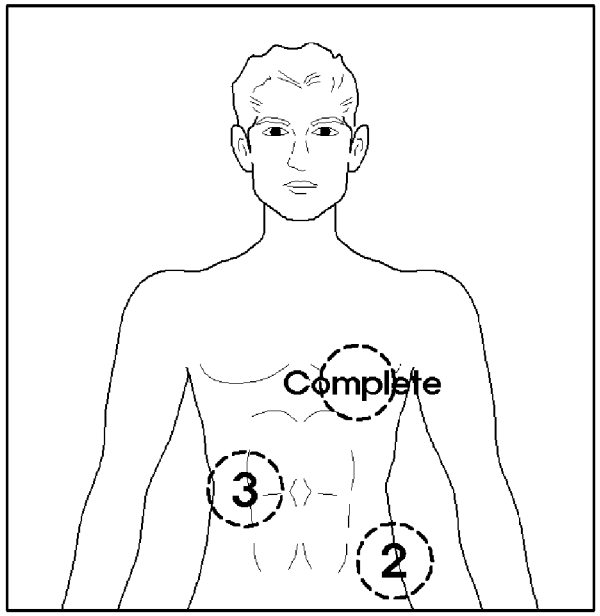
FIG. 29 is a view illustrating a third graphic user interface of the remote treatment method according to the seventh embodiment of the present invention.

Hereinafter, a remote treatment method according to a seventh embodiment of the present invention is described with reference to FIGS. 26, 27, 28, and 29. FIG. 26 is a flowchart illustrating the remote treatment method according to the seventh embodiment of the present invention, and FIGS. 27, 28, and 29 are views illustrating graphic user interfaces in the remote treatment method according to the seventh embodiment of the present invention.

The remote treatment method according to the seventh embodiment of the present invention may include a step of outputting an image of a treatment target (S710), a step of receiving information regarding a plurality of checkup parts (S720), a step of obtaining a plurality of first areas corresponding to the plurality of checkup parts in the image of the treatment target (S730), a step of displaying a plurality of first indicators on the plurality of first areas, respectively, to overlap the image of the treatment target (S740), a step of receiving information regarding a treatment order (S750), a step of displaying a fifth indicator reflecting the treatment order to each of the plurality of first areas (S760), and a step of deleting at least one of the first and fifth indicators corresponding to a treatment-completed checkup part (S770). Hereinafter, the steps included in the remote treatment method according to the seventh embodiment of the present invention are described.

First, the patient terminal 100 may output the image of the treatment target (S710). This may be the same as that in the remote treatment method according to the first embodiment of the present invention. The patient terminal 100 may receive the information regarding the plurality of checkup parts (S720). The communication unit 140 may receive the information regarding the plurality of checkup parts from the medical person terminal 200. The plurality of checkup parts may be, e.g., a right side of a chest, a right side of a pelvis, and a left side of a waist, as shown in FIG. 27.

The patient terminal 100 may obtain the plurality of first areas corresponding to the plurality of checkup parts in the image of the treatment target based on the information regarding the checkup part (S730). The controller 150 may determine the plurality of first areas corresponding to the plurality of checkup parts in the image of the treatment target. As described above, an area corresponding to a checkup part in the image of the treatment target may be determined by an augmented reality scheme. For example, a pattern of an image corresponding to a checkup part may be recognized and compared with a pattern of image of the treatment target, so that the plurality of first areas corresponding to the plurality of checkup parts may be determined.

The patient terminal 100 may control the output unit 120 to output the plurality of first indicators on the plurality of first areas, respectively, to overlap the image of the treatment target (S740). Here, the first indicators may reflect the plurality of checkup parts, respectively.

The patient terminal 100 may receive the information regarding the treatment order of the plurality of checkup parts (S750). Here, the communication unit 140 may receive the information regarding the treatment order for the plurality of checkup parts from the medical person terminal 200. Or, the controller 150 may generate the treatment order according to a predetermined program for the plurality of checkup parts.

The patient terminal 100 may display the fifth indicator reflecting the treatment order on each of the plurality of first areas (S760). The controller 150 may control the output unit 120 to display the fifth indicator on each of the plurality of first areas to overlap the output image of the treatment target. For example, the treatment order may be determined on the checkup parts, for example, in the order of a right side of a chest, a right side of a pelvis, and a left side of a waist, i.e., in the order of the chest, pelvis, and waist. At this time, the output unit 120 may display the fifth indicator reflecting the order on each first area as shown in FIG. 27.

Here, as described above in connection with the remote treatment method according to the first embodiment of the present invention, the output unit 120 may also display a second indicator reflecting the checkup tool 30, a third indicator reflecting a name of the checkup part, and a fourth indicator reflecting the type of the checkup tool 30. At this time, a plurality of sub-indicators may be included in each of the indicators.

The patient terminal 100 may delete at least one of the first and fifth indicators corresponding to a checkup part where the treatment has been done. The controller 150 may control the output unit 120 so that the output unit 120 does not any longer display an indicator corresponding to a checkup part where the treatment has been complete. For example, as shown in FIG. 27, if the right side of the chest has been done with the treatment, the controller 150 may control the output unit 120 so that the first and fifth indicators for the corresponding checkup part are deleted. Or, instead of allowing the indicator to be deleted with respect to the checkup part where the treatment has been complete, the patient terminal 100 may display information indicating that the treatment has been complete. For example, as shown in FIG. 28, if the right side of the chest is done with treatment, the controller 150 may control the output unit 120 to display information indicating that the treatment for the checkup part has been done on the first area corresponding to the checkup part.

By the remote treatment method according to the seventh embodiment of the present invention, the patient terminal 100 may provide information for guiding a manipulation of the checkup tool 30 with respect to the plurality of checkup parts. By doing so, a user may obtain more precise checkup data by manipulating the checkup tool 30 to be guided to a more precise position according to the treatment order.

Figure 30:
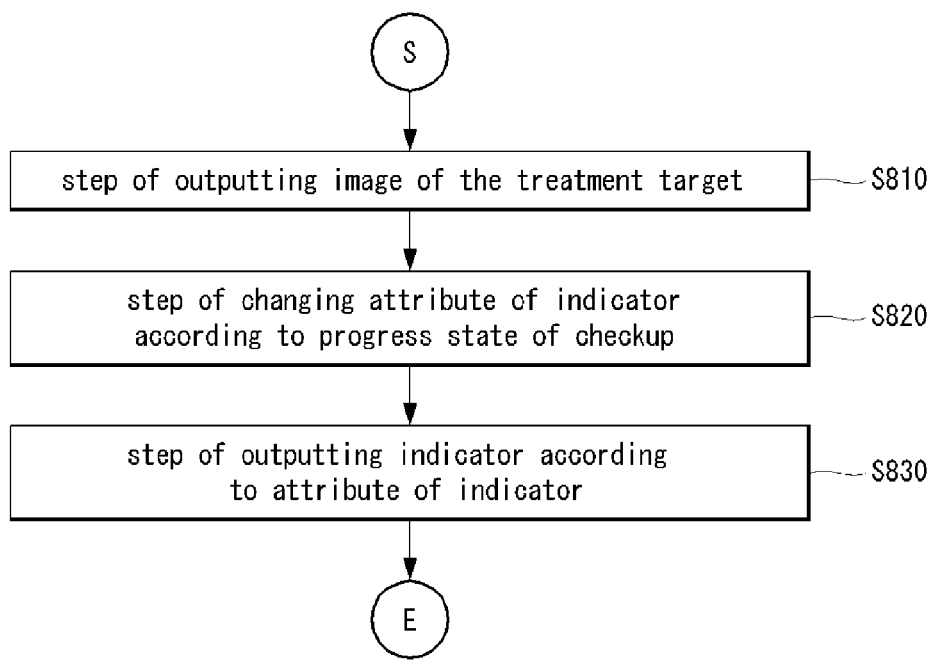
FIG. 30 is a flowchart illustrating a remote treatment method according to an eighth embodiment of the present invention.
Figure 31:
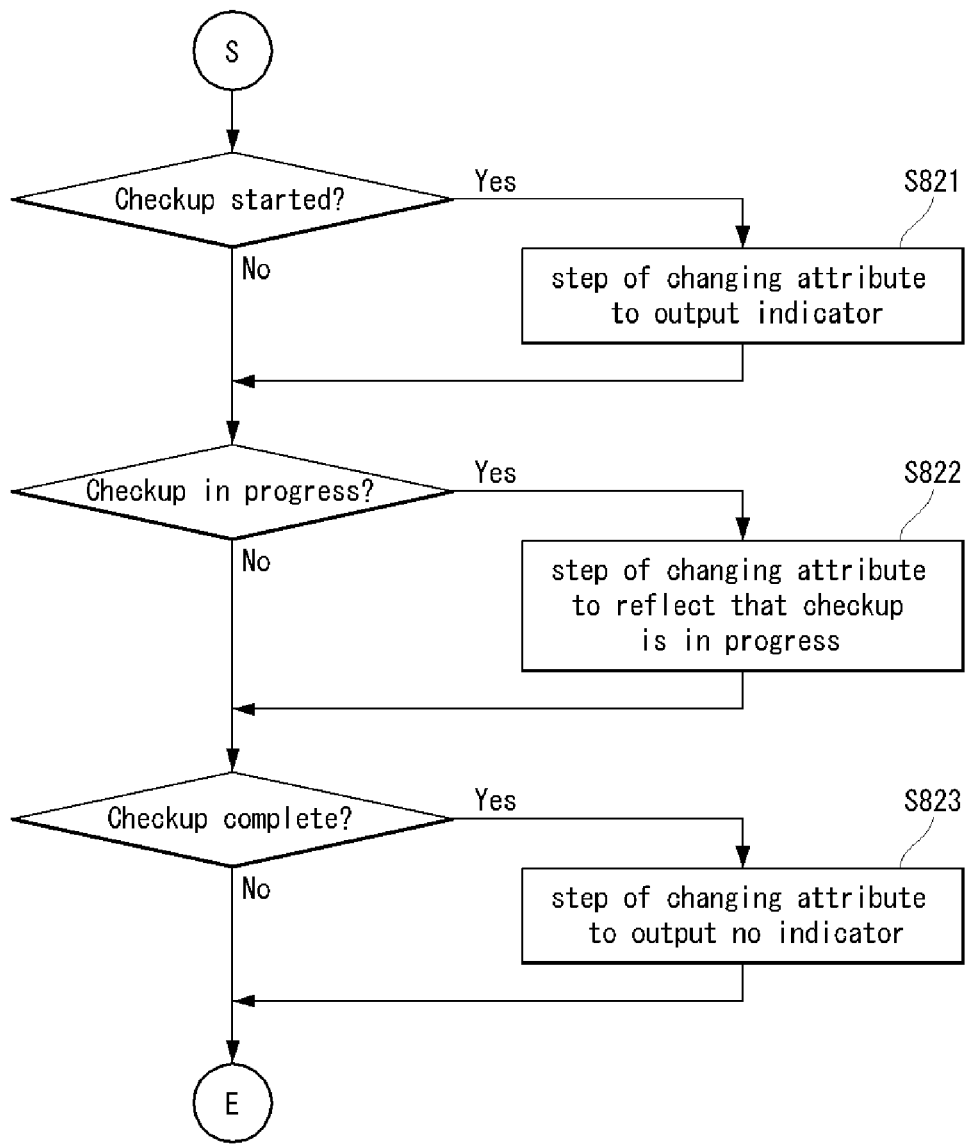
FIG. 31 is a flowchart illustrating a step of changing an attribute of an indicator in the remote treatment method according to the eighth embodiment of the present invention.

Hereinafter, a remote treatment method according to an eighth embodiment of the present invention is described with reference to FIGS. 3, 31, and 32. FIG. 30 is a flowchart illustrating the remote treatment method according to the eighth embodiment of the present invention, FIG. 31 is a flowchart illustrating a step of changing an attribute of an indicator in the remote treatment method according to the eighth embodiment of the present invention, and FIG. 32 is a view illustrating a first graphic user interface in the remote treatment method according to the eighth embodiment of the present invention.

The remote treatment method according to the eighth embodiment of the present invention may include a step of outputting an image of a treatment target (S810), a step of determining or changing an attribute of an indicator based on a progress state of a treatment performed on the treatment target (S820), and a step of displaying an indicator considering the attribute of the indicator reflecting the progress state of the treatment (S830). Hereinafter, the steps included in the remote treatment method according to the eighth embodiment of the present invention are described.

The step of outputting the image of the treatment target (S810) may be the same as that described above in connection with the remote treatment method according to the first embodiment of the present invention.

The patient terminal 100 may determine or change an attribute of an indicator based on a progress state of a treatment performed on the treatment target (S820). Here, the progress state of the treatment may include a state as to whether the treatment has been started, whether the treatment is in progress, whether the treatment has been abnormally terminated, whether a re-treatment is needed, or whether the treatment has been complete. As a specific example, upon reception of a signal indicating the start of the treatment by the communication unit 140, the treatment is initiated, and the treatment is in progress while the checkup tool 30 measures a checkup part, and if checkup data obtained by the checkup tool 30 is transmitted to the patient terminal 100, the treatment may be complete.

The controller 150 may determine or change the attribute of the indicator based on the progress state of the treatment. The attribute of the indicator may include, e.g., whether to output the indicator, and the position, shape, size, operation, color, and brightness of the indicator displayed. FIG. 31 is a flowchart illustrating an example where the attribute of the indicator is changed based on the progress state of the treatment. The controller 150 may change the attribute of the indicator so that the indicator is output when the progress of the treatment is started (S821). Here, the controller 150 may control the output unit 120 so that the indicator is output based on the attribute of the indicator indicating the output. Further, the controller 150 may change the attribute of the indicator so that the indicator reflecting that the treatment is in progress while the treatment is being conducted (S822). Accordingly, the output unit 120 may represent that the treatment is in progress by changing the shape, size, color, or operation of the indicator. For example, the output indicator may change its color as the treatment is in progress. Further, when the treatment is completed, the controller 150 may change the attribute of the indicator so that the indicator is not output (S823). Or, the controller 150 may change the attribute of the indicator so that when the treatment is completed, whether the treatment is completed is reflected. Accordingly, the output unit 120 may display no indicator or an indicator indicating that the treatment has been complete.

The patient terminal 100 may display an indicator considering the attribute of the indicator. The controller 150 may control the output unit 120 to output an indicator or not in consideration of the attribute of the indicator. Accordingly, the output unit 120 may display the indicator together with the image of the treatment target. For example, the output unit 120 may display the indicator at a predetermined point on the image of the treatment target. As another example, the output unit 120 may display the indicator separately from the image of the treatment target. Here, information regarding a position where the attribute of the indicator is output may be further provided. The controller 150 may control the output unit 120 considering the information regarding the position where the attribute of the indicator is output to thereby determine a position of output of the indicator.

As such, the output unit 120 may provide an indicator reflecting a progress state of a treatment to a user, so that the user may figure out the progress state of the treatment, thereby resulting in the treatment being performed more smoothly.

Figure 33:
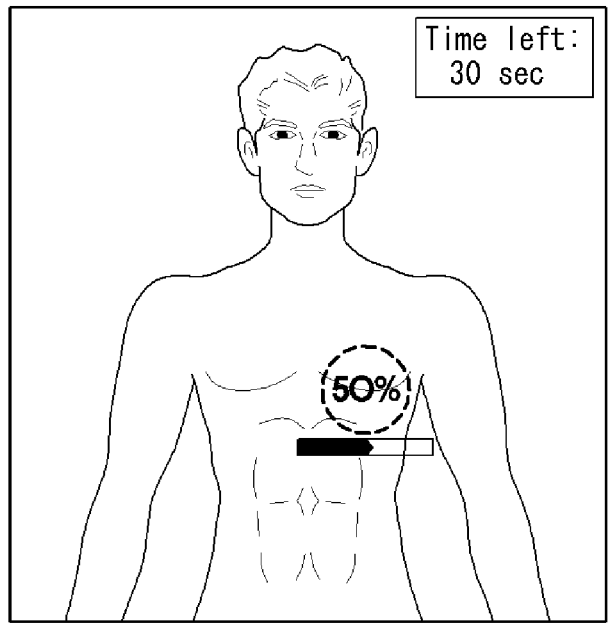
FIG. 33 is a view illustrating a second graphic user interface of the remote treatment method according to the eighth embodiment of the present invention.
Figure 34:
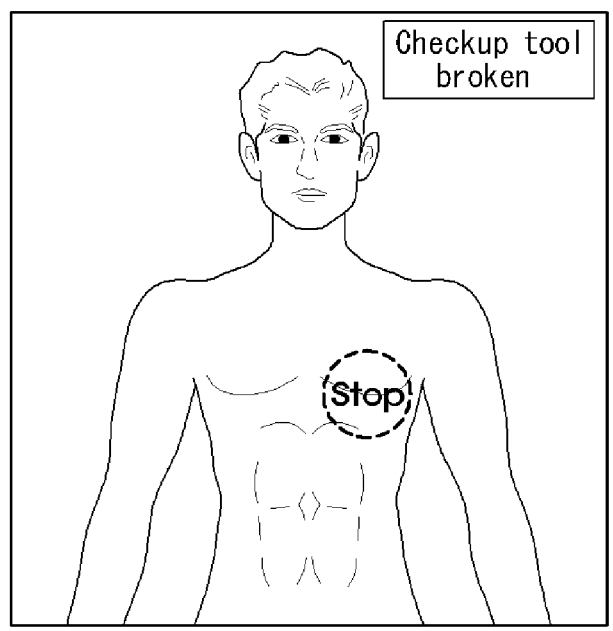
FIG. 34 is a view illustrating a third graphic user interface of the remote treatment method according to the eighth embodiment of the present invention.

Hereinafter, in the remote treatment method according to the eighth embodiment of the present invention, the indicator and the attribute of the indicator are described with reference to FIGS. 32, 33, 34, and 35. FIGS. 32, 33, and 34, respectively, are views illustrating graphic user interfaces in the remote treatment method according to the eighth embodiment of the present invention.

The indicator according to the eighth embodiment of the present invention may reflect information regarding a treatment. For example, the indicator may reflect a progress state of a checkup. Here, the attribute of the indicator may include information regarding whether to output the indicator, when the indicator is output, where the indicator is output, the color, shape, brightness, size, type, and operation of the indicator.

As shown in FIG. 32, based on whether the treatment is started, is in progress, or is completed, the output unit 120 of the patient terminal 100 may output the indicator reflecting the same or not.

When the treatment is in progress as shown in FIG. 33, the patient terminal 100 may indicate that the treatment is in progress. The output unit 120 may display a progress rate of the treatment or at least one of the time during which the treatment has been performed or a remaining time of the treatment. By doing so, a user may recognize how much the treatment has been performed and how further the treatment needs to be done at a glance.

When the treatment is abnormally terminated as shown in FIG. 34, the patient terminal 100 may indicate that the treatment is terminated. The output unit 120 may indicate that the treatment has been terminated or a cause of the termination of the treatment. By doing so, a user may be alerted to occurrence of an error while a remote treatment is in progress and may respond to the error.

Figure 35:
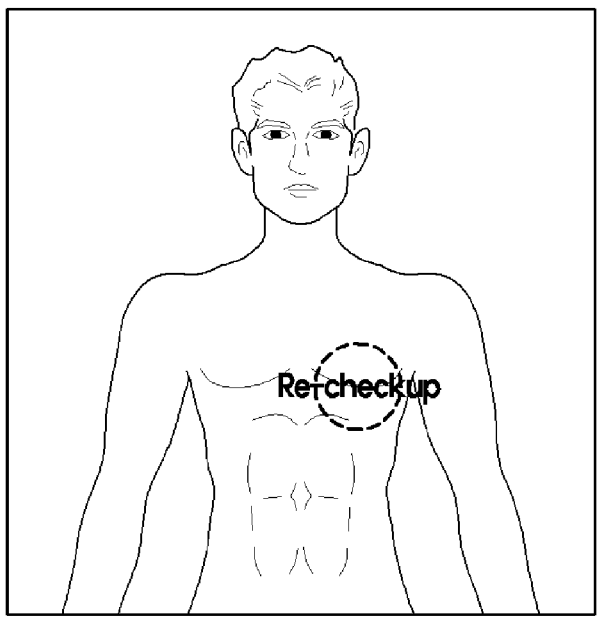
FIG. 35 is a view illustrating a fourth graphic user interface of the remote treatment method according to the eighth embodiment of the present invention.

When receiving a signal requesting a re-treatment from the medical person terminal 200 or when the treatment is abnormally diagnosed as shown in FIG. 35, the patient terminal 100 may output an indicator indicating a re-treatment. By doing so, a medical person may be easily indicated to re-treat a patient.

Figure 36:
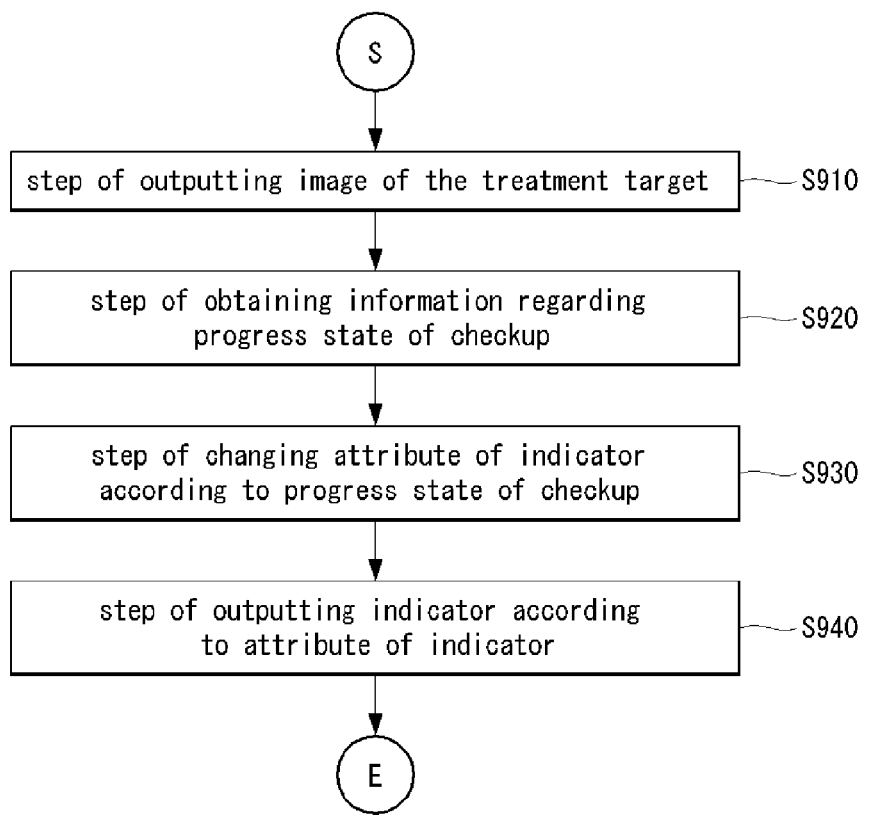
FIG. 36 is a flowchart illustrating a remote treatment method according to a ninth embodiment of the present invention.

Hereinafter, a remote treatment method according to a ninth embodiment of the present invention is described with reference to FIG. 36. FIG. 36 is a flowchart illustrating the remote treatment method according to the ninth embodiment of the present invention.

The remote treatment method according to the ninth embodiment of the present invention may include a step of outputting an image of a treatment target (S910), a step of obtaining information regarding a progress state of the treatment for the transmit (S920), a step of determining or changing an attribute of an indicator based on the progress state of the treatment (S930), and a step of displaying the indicator considering the attribute of the indicator reflecting the progress state of the treatment. Hereinafter, the steps included in the remote treatment method according to the ninth embodiment of the present invention are described.

The step of outputting the image of the treatment target (S910), the step of determining or changing the attribute of the indicator based on the progress state of the treatment (S930), and the step of displaying the indicator considering the attribute of the indicator reflecting the progress state of the treatment (S940) may be the same as those described above in connection with the remote treatment method according to the eighth embodiment of the present invention.

The patient terminal 100 may obtain the information regarding the progress state of the treatment for the treatment target (S920). The patient terminal 100 may obtain the information regarding the progress state of the treatment for the treatment target by various methods.

The communication unit 140 may receive the information regarding the progress state of the treatment from, e.g., the medical person terminal 200. For example, the medical person terminal 200 may receive an input indicating the start or complete of the treatment from the medical person and may transmit a signal according to the input to the patient terminal 100. Here, the information regarding the progress state of the treatment may further include information regarding a checkup part. Accordingly, the controller 150 may control the output unit 120 so that the indicator is displayed at a position corresponding to the checkup part in the image of the treatment target.

Or, the input unit 110 may receive an input regarding the progress state of the treatment from a user. Here, the user may include the treatment target or a U-health nurse who helps the treatment target. For example, the input unit 110 may receive an input indicating the start of the treatment from the user.

Or, the communication unit 140 may receive information indicating the progress state of the treatment from the checkup tool 30. For example, the patient terminal 100 may receive information indicating that the treatment is in progress from an electronic stethoscope or information indicating that the treatment is started or complete. Or, the patient terminal 100 may receive a signal indicating that the checkup tool 30 is out of order while the treatment is being conducted from an electronic thermometer.

Or, the communication unit 140 may receive checkup data from the checkup tool 30, and the controller 150 may determine the progress state of the treatment based on the received checkup data. Here, the progress state of the treatment may include the treatment being started, underway, or terminated, and a progress rate of the treatment. For example, in case a one minute-long stethoscopic sound needs to be received from an electronic stethoscope, if the communication unit 140 receives a 30 second-long stethoscopic sound, the controller 150 may determine, based on the length of the received stethoscopic sound, that the treatment has been 50% and another 30 seconds remain. Further, when a one minute-long stethoscope sound is received, the controller 150 may determine that the auscultation has been complete. Further, if the patient terminal 100 fails to receive the whole checkup data from the checkup tool 30 when terminating communication with the checkup tool 30, the controller 150 may determine that an error has occurred. The output unit 120 may Output an indicator indicating at least one of the fact that the error has occurred and a cause of the error. Or, the output unit 120 may output an indicator indicating a re-treatment.

By such methods, the patient terminal 100 may obtain the information regarding the progress state.

The remote treatment methods according to the first to ninth embodiments of the present invention as described above may be performed alone or in combination. Further, the steps constituting an embodiment may be performed separately from or in combination with the steps constituting another embodiment.

By the remote treatment methods according to the present invention, a medical person and a patient may perform a remote treatment more effectively. Accordingly, one may stay healthier, and may save unnecessary medical costs.

According to the present invention, there are provided a remote treatment method and an electronic device that may mark a checkup part on an image of a treatment target to guide a manipulation of a checkup tool, so that a user may perform a treatment according to the mark of the checkup part even without specialized knowledge on the checkup tool.

Although the embodiments of the present invention have been described, it is understood by those skilled in the art that various modifications and variations may be made to the present invention without departing from the scope or spirit of the present invention. All or some of the embodiments may be selectively combined.

What is claimed is:

1. An electronic device comprising:
    an output unit configured to output an image of a treatment target;
    a communication unit configured to receive treatment information including a checkup part and information regarding a progress state of a remote treatment for the treatment target from at least one of an external device or a checkup tool; and
    a controller configured to:
        obtain a first area corresponding to the checkup part of the image of the treatment target;
        display a first indicator indicating the checkup part, a second indicator indicating a name of the checkup part, and a third indicator indicating a type of the checkup tool on the first area;
        display a fourth indicator reflecting the progress state considering an attribute of the fourth indicator; and
        change the attribute of the fourth indicator based on the progress state,
    wherein the progress state of the remote treatment includes whether the remote treatment has been started, whether the remote treatment is in progress, whether the remote treatment has been abnormally terminated and whether a re-treatment is needed.

2. The electronic device of claim 1, further comprising an input unit configured to receive information regarding the progress state of the treatment.

3. The electronic device of claim 1,
    wherein the controller is configured to determine the progress state of the treatment based on the received checkup data.

4. The electronic device of claim 1, wherein the attribute of the fourth indicator includes information regarding at least one of whether to output the fourth indicator, and a position of output, a color, a brightness, a shape, and a size of the fourth indicator.

5. The electronic device of claim 1, wherein the controller is configured to change the attribute of the fourth indicator so that the fourth indicator is output when the treatment is started.

6. The electronic device of claim 1, wherein the controller is configured to change the attribute of the fourth indicator so that the fourth indicator indicates that the treatment is in progress when the treatment is being performed.

7. The electronic device of claim 6, wherein the controller is configured to change the attribute of the fourth indicator so that the fourth indicator indicates at least one of a progress rate of the treatment and a remaining time of the treatment when the treatment is in progress.

8. The electronic device of claim 1, wherein the controller is configured to change the attribute of the fourth indicator so that when an error occurs during the treatment, the fourth indicator indicates at least one of occurrence of the error and a cause of the error.

9. The electronic device of claim 1, wherein the controller is configured to change the attribute of the fourth indicator so that when an error occurs during the treatment or upon receiving a request for a re-treatment, the fourth indicator indicates the re-treatment.

10. The electronic device of claim 1, wherein the controller is configured to change the attribute of the fourth indicator so that when the treatment is completed, the fourth indicator indicates that the treatment is completed.

11. The electronic device of claim 1, wherein the controller is configured to change the attribute of the fourth indicator so that when the treatment is completed, the fourth indicator is not output.

12. The electronic device of claim 1, wherein the attribute of the fourth indicator includes information regarding an output position of the fourth indicator, wherein the output position is a position corresponding to the checkup part in the image of the treatment target, and wherein the controller is configured to control the output unit so that the fourth indicator is displayed to overlap the image of the treatment target.

13. The electronic device of claim 1,
wherein the controller is configured to receive checkup data regarding the checkup part displayed by the fourth indicator from the checkup tool through the communication unit and output the checkup data on the output unit.

14. The electronic device of claim 13, wherein the checkup data includes at least one of bio-information measured from the checkup part and an affected part image obtained by capturing the checkup part.

15. The electronic device of claim 14, wherein the affected part image includes a plurality of partial images obtained by capturing at least a portion of the checkup part, and wherein the controller is configured to combine the plurality of partial images to generate a whole image for the checkup part.

16. The electronic device of claim 13, wherein the communication unit is configured to transmit the checkup data to an external device.

17. The electronic device of claim 13, further comprising a camera configured to capture the image of the treatment target.

18. The electronic device of claim 13, further comprising a storage unit configured to store at least a portion of the image of the treatment target.

19. The electronic device of claim 18, wherein the stored at least the portion of the image of the treatment target includes at least one of a video and a still image.

20. A remote treatment method comprising:
displaying an image of a treatment target on an output unit;
receiving treatment information including a checkup part and information regarding a progress state of a remote treatment for the treatment target from at least one of an external device or a checkup tool;
obtaining a first area corresponding to the checkup part of the image of the treatment target;
displaying a first indicator indicating the checkup part, a second indicator indicating a name of the checkup part, and a third indicator indicating a type of the checkup tool on the first area;
displaying a fourth indicator reflecting the progress state of the treatment for the treatment target together with the image considering an attribute of the fourth indicator on the output unit; and
changing the attribute of the fourth indicator based on the progress state of the treatment for the treatment target,
wherein the progress state of the remote treatment includes whether the remote treatment has been started, whether the remote treatment is in progress, whether the remote treatment has been abnormally terminated and whether a re-treatment is needed.

* * * * *